(12) United States Patent
Baker et al.

(10) Patent No.: US 6,353,112 B1
(45) Date of Patent: Mar. 5, 2002

(54) SULTAMS: SOLID PHASE AND OTHER SYNTHESIS OF ANTI-HIV COMPOUNDS AND COMPOSITIONS

(75) Inventors: David C. Baker, Knoxville, TN (US); Bin Jiang, King of Prussia, PA (US)

(73) Assignee: The University of Tennessee Research Corporation, Knoxville, TN (US)

(*) Notice: Subject to any disclaimer, the term of this patent is extended or adjusted under 35 U.S.C. 154(b) by 0 days.

(21) Appl. No.: 09/314,339

(22) Filed: May 19, 1999

Related U.S. Application Data

(60) Provisional application No. 60/097,225, filed on Aug. 20, 1998, and provisional application No. 60/093,167, filed on Jul. 17, 1998.

(51) Int. Cl.⁷ .......................................... C07D 275/06
(52) U.S. Cl. ..................................................... 548/207
(58) Field of Search ........................................ 548/207

(56) References Cited

FOREIGN PATENT DOCUMENTS

| DE | 2105580 | 2/1971 |
| WO | WO 98/42643 | 1/1998 |
| WO | WO 00/18708 | 4/2000 |

OTHER PUBLICATIONS

Mashima, et al. Asymmetric Transfer Hydrogenation of Ketonic Substrates Catalyzed by (n5–C5Me5)MCl Complexes {M–Rh and Ir} of (1S,2S)–N–(p–Toluenesulfonyl)–1,2–diphenylethylenediamine. Chemistry Letters. Dec. 1998, No. 12, pp. 1199–1200.

Mashima, et al. The Half–sandwich Hydride and 16–Electron Complexes of Rhodium and Iridium Containing (1S, 2S)–N–(p–Toluenesulfonyl)–1,2–diphenylethylenediamine: Relevant to the Asymmetric Transfer Hydrogenation. Chemistry Letters. Dec. 1998, No. 12, pp. 1201–1202.

Buchwald, Stephen L et al. Recent Progress in the Suzuki Reactions of Aryl Chlorides. The Strem Chemiker, May 2000, vol. XVIII, No. 1.

Mao, Jianmin et al. A Chiral Rhodium Complex for Rapid Asymmetric Transfer Hydrogenation of Imines with High Enantioselectivity. Organic Letters, May 24, 1999, vol. 1, No. 6, pp. 841–843.

*Primary Examiner*—Robert Gerstl
(74) *Attorney, Agent, or Firm*—Schnader Harrison Segal & Lewis LLP

(57) ABSTRACT

Biologically active sultams are disclosed which have potent anti-HIV activity. A combinational method of synthesis, which uses a solid support and variants thereof, are described. Biological compositions and method of treating mammals for viral infections with compositions comprising the sultams of the invention, especially HIV are described.

27 Claims, 6 Drawing Sheets

SULTAMS: SOLID PHASE AND OTHER SYNTHESIS OF ANTI-HIV COMPOUNDS AND COMPOSITIONS

CROSS-REFERENCE TO RELATED PATENT APPLICATIONS

This application is based on two earlier filed provisional patent applications filed under 37 C.F.R. 1.53(b)(2), application Ser. No. 60/093,167 filed on Jul. 17, 1998 entitled Synthesis an Modification of 2,3-Dihydrobenzo[d] isothaizoles, and application Ser. No.60/097,225 filed on Aug. 20, 1998 entitled A Solid-Phase Synthesis and Combinatorial Approach to 2,3-Dihydrobenzo[d]isothaizoles 1,1-dioxides that are Substituted at the 2- and/or 3-Positions. This application claims the benefit of the filing dates of these two applications. These applications are incorporated herein by reference in their entirety.

STATEMENT REGARDING FEDERALLY SUPPORTED RESEARCH

This invention was made with government support under Contract/Grant N01-CM-67261 awarded by the National Cancer Institute. The government has certain rights in this invention.

BACKGROUND OF THE INVENTION

In 1982 physicians first became aware of a new sexually transmitted disease that was associated with an unusual form of cancer (Kaposi's sarcoma) and a variety of unusual infections. The disease was named acquired immune deficiency syndrome (AIDS), since both these problems reflected a severe deficiency in the helper T cells of the immune system. A retrovirus, called human immunodeficiency virus (HIV), was found to be the causative agent of AIDS.

HIV is a member of a family of viruses called lentiviruses that are part of a large group of viruses known as the Retroviridae. Some of the other members of the group are the closely related simian, feline and bovine immunodeficiency viruses. This group of viruses displays a variety of common features.

The fact that HIV has an extreme tendency to mutate to forms that are resistant to existing antiviral therapies greatly complicates attempts to treat the infection with antiviral drugs. Most of the current research in AIDS is aimed at understanding the life cycle of HIV. AIDS research has been targeted towards inhibition of the virus at different stages of its life cycle.

The molecular target for HIV inhibitors can be broadly classified into the following classes: reverse transcriptase (RT) enzyme, protease enzyme, integrase enzyme, regulatory proteins, and zinc finger domains in the nucleocapsid p7 protein.

The normal flow of genetic information is from DNA to RNA to protein, and hence HIV, which is a retrovirus, must first convert its genomic RNA into a double-stranded DNA in order to start its replication cycle in the host cell. This conversion takes place in the host cell cytoplasm with the help of a viral enzyme called reverse transcriptase (RT) that catalyzes a series of biochemical reactions involved in this process. This makes reverse transcriptase (RT) enzyme an attractive target for HIV inhibitors. HIV RT inhibitors can be broadly classified into nucleoside (NRTIs) and non-nucleoside RT inhibitors (NNRTIs). The modes of action of these two classes of compounds are different in nature. The nucleoside HIV RT inhibitors are competitive inhibitors that to bind to the catalytic site of the enzyme, and their mode of action appears to be through their triphosphates (produced in the cytoplasm of the host cell) that act as RT enzyme inhibitors through incorporation and termination of the growing viral DNA chain. Common nucleoside RT inhibitors are AZT, ddC, ddI, d4T, 3TC, and Abacavir.

This invention deals with non-nucleoside RT inhibitors. Non-nucleoside reverse transcriptase inhibitors (NNRTIs) are non-competitive inhibitors of the RT enzyme; they bind to an allosteric (regulatory) site with a degree of magnitude heretofore not yet observed and influence the RT catalytic site. Hence, they are also referred to as second-site RT inhibitors. In general, at micromolar concentrations NNRTIs inhibit HIV-1 in vitro with minimum or no cytotoxicity but do not inhibit HIV-2 or other retroviruses. Some non-nucleoside RT inhibitors are chloro-TIBO, nevirapine, L-697,661, and delavirdine.

1. Field of the Invention

The need and research for active inhibitors of human immunodeficiency virus-1 reverse transcriptase (HIV-1 RT) is urgent and ongoing. In 1997, U.S. Pat. No. 5,608,085 issued to Baker et al. discloses a Synthesis of Optically Active Calanolides A and B and Enantiomers and Related Compounds, which produces anti-HIV-1 or HIV-2 compounds in high yields and in a high degree of purity. Recently, on Dec. 1, 1998, U.S. Pat. No. 5,843,990 issued to Baker et al. entitled Pyran-Chromenone Compounds, Their Synthesis and Anti-HIV Activity, which deals with a class of compounds, particularly optically active compounds of a high degree of purity and free of the corresponding enantiomers, which are highly potent anti-HIV compounds (Ref 25). In accordance with this invention, novel 2,3-dihydrobenzo[d]isothiazole 1,1-dioxides (sultams) have been discovered that are biologically active, particularly potent HIV reverse-transcriptase inhibitors. Further, a novel solid-phase combinatorial synthesis has been discovered in which a solid support is used.

Combinatorial organic synthesis (COS) is a known methodology for creating huge, searchable libraries of small organic molecules suitable for both drug-discovery screening and drug-development optimization. Frequently, the use of a solid support in the synthesis will usually eliminate the need for difficult-to-automate procedures like extractions, filtrations and chromatography. Multistep syntheses are typically carried out to completion without purification of the products at intermediate stages. Further, the use of a solid support facilitates the use of a split-pool technique, which offers the most efficient manner of synthesizing large libraries ($10^3$–$10^9$ compounds). Combinatorial chemistry processes commonly use automation which provides several advantages: First, automated systems perform functions that are impossible to do by hand, such as delivering exceedingly small volume of liquids to precise locations. Second, the consistency of an errorless process can be enhanced. Third, and perhaps more important, an appropriately designed automated system will perform functions quickly and repeatedly with consistency of quality and output over long periods of time.

The invention lends itself to the use of a solid support and of combinatorial synthesis.

2. Description of Related Art

Publications of interest relating to the subject matter of this invention include:

1. Borman, S., "Combinatorial Chemistry", special report, *C&EN News*, page 47, Apr. 6, 1998.

2. Chaiken, I. M.; Janda, K. D., Eds.; *Molecular Diversity and Combinatorial Chemistry;* American Chemical Society: Washington, D.C., 1996.
3. Wilson, S. R.; Czarnik, A. W., *Combinatorial Chemistry;* John Wiley & Sons, Inc., New York, 1997.
4. Gulakowski et al., *J. Virol. Meth.* 1991, 33, 87–100.
5. Gordon, E. M.; Kerwin, J. F. Jr., *Combinatorial Chemistry And Molecular Diversity in Drug Discovery,* John Wiley & Sons, Inc.: New York, 1998.
6. Hermkens, P. H. H.; Ottenheijm, H. C. J.; Reeds, D., *Tetrahedron,* 1996, 52, 4527–4554.
7. Hermkens, P. H. H.; Ottenheijm, H. C. J.; Reeds, D., *Tetrahedron,* 1997, 53, 5643–5678.
8. Watanabe, H.; Gay, R. L.; Hauser, C. R., *J. Org. Chem.* 1968, 33, 900–903.
9. Plunkett, M.; Ellman, J. A., *J. Org. Chem.,* 1997, 62, 2885–2893.
10. Woolard, F. X.; Paetsch, J.; Ellman, J. A. *J. Org. Chem.,* 1997, 62, 6102–6103.
11. Beaver, K. A., Siegmund, A. C.; Spear, K. L., *Tetrahedron,* 1996, 37, 1145–1148.
12. Halm, C., Evarts, J. and Kurth, M. J. *Tetrahedron lets.,* 1997, 38, 7709–7712.
13. Seeberger, P. H., Beebe, X., Sukenick, G. D., Pochapsky, S. and Danishefsky, S. J. *Angew. Chem., Int. Ed. Engl,* 1997, 36, 491–493.
14. Kim, S. W.; Hong, C. Y.; Lee, K.; Lee, E. J.; Koh, J. S. *Bioorg. Med Chem. Lett.,* 1998, 8, 735–738.
15. Beaver, K. A. et al.; U.S. Pat. No. 4,859,736; 1989.
16. Nicolaou, K. C.; Xiao, X.-Y.; Pasandoosh, Z; Senyei, A.; Nova, M. P. *Angew. Chem., Int. Ed. Engl.,* 1995, 34, 2289–2291.
17. Moran, E. J.; Sarshar, S.; Cargill, J. F.; Shahbaz, M. M.; Lio, A.; Mjalli, A. M. M. Armstrong, R. W. *J. Am. Chem. Soc.,* 1995, 117, 10787–10788.
18. European patent application No. O 422 944 A1, published on Apr. 17, 1991, entitled *Chiral Sultams.*
19. Snieckus, V., *Chemical Synthesis: Gnosis to Prognosis,* Chatagilialoglu, C.; Snieckus, V. Eds.; Kluwer Academic Publishers: Dordrecht, 1996, pp 191–221.
20. Alerton, E. et al., *Proc. Am. Pept. Symp.* pp 163–195. Pierce Chemical Company: Rockford, Ill. (1981).
21. Weislow, O. W. et al., *J. Natl. Cancer Inst.,* 1989, 81, 577–586.
22. Eliel, E. L.; Wilen, S. H. *Stereochemistry of Organic Compounds,* John Wiley & Sons Inc.: New York, 1994.
23. *Remington's Pharmaceutical Sciences,* Mack Publishing Co., Easton, Pa., USA.
24. Corbett, J. W. *Org. Prep. Proc. Int.,* 1998, 30, 489–550.
25. Deshpande, P. P.; Tagliaferri, F.; Victory, S. F.; Yan, S.; Baker, D. C. *J. Org. Chem.* 1995, 60, 2964–2965.
26. Watanabe et al., *J. Org. Chem.* 1968, 33,900–903; DeClercq, E. *Med. Res. Rev.* 1993, 13, 229.
27. DeClercq, E. *Med. Res. Rev.* 1993, 13, 229.
28. Kilby, M. J.; Saag, M. S. In *Antiviral Chemotherapy 4: New Directions for Clinical Application and Research;* Mills, J.; Volberding, P. A.; Corey, L., Eds.; Plenum Press: New York, 1996, pp 291–298.
29. Romero, D. L.; Morge, R. A.; Genin, M. J.; Biles, C.; Busso, M.; Resnick, L.; Altaus, I. W.; Reusser, F.; Thomas, R. C.; Tarpley, W. G. *J. Med. Chem.* 1993, 36, 1505.
30. Dueweke, T. J.; Poppe, S. M.; Romero, D. L.; Swaney, S. M.; So, A. G.; Downey, K. M.; Althaus, I. W.; Reusser, F.; Busso, M.; Resnick, L.; Mayers, D. L.; Lane, J.; Aristoff, P. A.; Thomas, R. C.; Tarpley, W. G. *Antimicrob. Agents Chemother.* 1993, 37, 1127.
31. Vasudevachari, M. B.; Battista, C.; Lane, H. C.; Psallidopoulos, M. C.; Zhao, B.; Cook, J.; Palmer, J. R.; Romero, D. L.; Tarpley, W. G.; Salzman, N. P. *Virology,* 1992, 190, 269.
32. Merluzzi, V. J.; Hargrave, K. D.; Labadia, M.; Grozinger, K.; Skoog, M.; Wu, J. C.; Shih, C. K.; Eckner, K.; Hattox, S.; Adams, J.; Rosehthal, S. A.; Frances, R.; Eckner, R. J.; Koup, R. A.; Sullivan, J. L. *Science* 1990, 250, 1411.
33. Lehninger, A. L.; Nelson, D. L.; Cox, M. M. *Principles of Biochemistry,* Second Edition, Worth Publishers, N.Y., N.Y., 1992

All references referred to in this text are incorporated herein by reference in their entirety.

BRIEF SUMMARY OF THE INVENTION

The invention relates to a new class of compounds herein identified generally as sultams, which may be represented by the following formula VI, in which the numbering of the atoms is started with the sulfur atom of the isothiazole. Two of the rings (ring A and C) are aromatic, and the third is a heterocyclic ring (ring B), a cyclic sulfonamide.

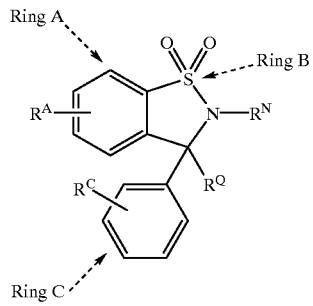

VI

Sultams are derivates of isothiazole 1,1-dioxide (cyclic 5-membered sulfonamides) with an aromatic ring fused at the C-4 and C-5 positions of the isothiazole ring. The investigated sultams have various substituents on the aromatic rings. The nitrogen of the sulfonamide is either tertiary or secondary depending on the nature of the substituents on that atom. On the C-3 position of sultams a variety of aromatic substituents are possible depending whether aldehydes or ketones are used in the synthesis. The other substituents on the same carbon can either be hydrogen, when an aldehyde is the reactant, or another substituent defined further below. This carbon, which has four ligands, or three ligands and hydrogen, is asymmetric, and thus determines the chirality of the resulted sultams. A racemic substance comprised of a pair of enantiomers is generally the product of synthesis, which substance can be resolved into the respective enantiomers.

The invention provides several methods of synthesis of the compounds of the invention, in particular a synthesis which uses a solid phase (or support), which allows readily the construction of a combinatorial library. The invention also provides such a combinatorial synthesis that can be carried out by automation. Such solid-phase syntheses have been described in the review article by Corbett (ref 24).

Several difficulties were encountered when attempts were made to use methods available in the literature to make ring compounds in racemic form. Ultimately, a synthesis was developed in which the nitrogen atom of the compounds remains linked throughout the synthesis to a solid support until its removal concurrently with closure of ring B.

Synthesis variations are also taught by the invention that provide a variety of substituents on the rings of the compounds. One such synthesis yields compounds wherein $R^N$ is hydrogen. Another synthesis provided by the invention that does not need to use a solid support yields compounds in which all substituents R are hydrogens. Another synthesis variation provided by the invention that can be performed with or without a solid support, yields compounds wherein $R^Q$ is $CF_3$. Other variations are described hereafter.

An objective of the synthesis was to obtain biologically active compounds, especially anti-HIV compounds. The sultam compounds of the invention offer the possibility of a variety of structural modifications and various possibilities of positioning of different substituents in different positions on any one of the rings. It was not known prior to this invention what effect these various substituents and their different positions on the nitrogen, on the stereogenic carbon, and on the ring(s) would have on their biological and more particularly their anti-HIV activity.

The invention also provides a new class of such compounds in racemic form that can be resolved into their respective enantiomers. A group of these compounds has an anti-HIV potency heretofore unachieved with this class of compound. In accordance with the invention, an area of the molecule has been identified on which appropriate substituents appear to make a major combination to a high degree of anti-HIV potency.

The invention also provides a method for alleviating, treating or preventing viral infections, especially strains of the HIV virus.

The invention also provides biologically active compositions which comprise one or more compounds of the invention, in an effective, nontoxic amount in combination with a biologically or pharmaceutically acceptable carrier.

The invention also provides drug combinations of compounds of the invention with HIV protease inhibitors, like ritonavir, saquinavir mesylate, and others.

In still another aspect, the invention provides a method for treating a mammal, particularly a human, infected with a retrovirus, which comprises administering to said mammal in need of such treatment an effective nontoxic amount of the composition(s) of the intention.

In summary, the invention contributes to solve a serious and urgent worldwide health need which has adverse social and economic consequences.

DETAILED DESCRIPTION OF THE INVENTION

The Compounds of the Invention

Figure 1:
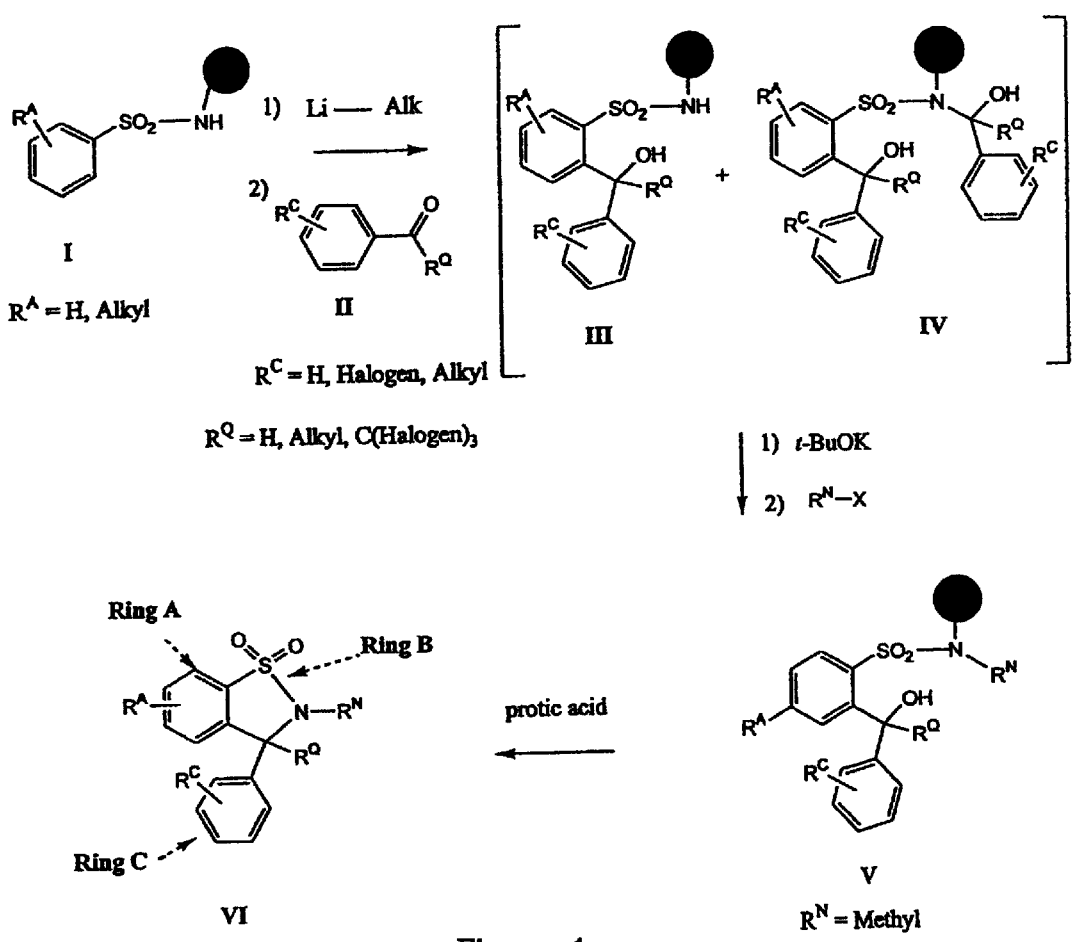
FIG. 1 shows a general scheme of the synthesis of sultams.

The sultams of the invention includes the compounds of formula VI, in which $R^A$ is hydrogen, a linear- or a branched-chain hydrocarbon (saturated or unsaturated) like alkyl preferably lower alkyl, a halogen like chloro-, bromo-, iodo or fluoro.

$R^N$ is hydrogen, a linear- or branched-hydrocarbon (saturated or unsaturated) like alkyl, preferably lower alkyl.

$R^Q$ is hydrogen, a linear- or branched-hydrocarbon (saturated or unsaturated), like alkyl, preferably lower alkyl, a substituted alkyl like $CF_3$, aryl, alkyl-substituted aryl, a heterocyclic structure, like pyridinyl, picolinyl, where the heteroatoms can be nitrogen, oxygen or sulfur, and fused rings like naphthyl, or quinolinyl.

$R^C$ is hydrogen, a linear- or branched-hydrocarbon (saturated or unsaturated), like alkyl, preferably lower alkyl, a halogen substituent like chloro-, bromo-, iodo- or fluoro-; hydroxyl, alkoxyl, preferably lower alkoxyl, an amide like an acylamide or lower alkyl, preferably containing not more than six carbons.

Other than a benzene ring, ring A can also be a heterocyclic like furyl or a polycyclic ring providing it generates only one single species upon ortho lithiation with an alkyl lithium as opposed to isomers. For example, 4$SO_2$NH-Resin substituted pyridine (I in FIG. 1) could be ortho-lithiated only at the 3-position of pyridine (numbered from the nitrogen). Preferably, the polycyclic ring has carbon atoms, and when it is a heterocylic ring, the heteroatoms can be nitrogen or sulfur.

Ring C can also be a heterocyclic or polycyclic aromatic ring providing the corresponding aldehyde or ketone is sufficiently reactive in the reaction. An aliphatic aldehyde can also be used, resulting in a sultam with an aliphatic substituent rather than an aromatic C ring.

The sultam in which all substituents are hydrogen but for $R^N$ which is methyl, namely (±)-2-methyl-3-phenyl-2,3-dihydrobenzo[d]isothiazole 1,1-dioxide, is a known compound. Ref. 26. The compound is included among the compounds made by the synthesis of the invention because, as far as is known, it had never been made by this method.

The Method of the Invention

The invention also provides a synthesis using a solid phase which allows ready construction of a combinatorial library. As described hereinafter, various different solid supports can be used. Presently preferred, one is a copolymer of chloro[chloromethyl-copoly(styrene-divinylbenzene) with 4-(2',4'-dimethoxyphenyl-Fmoc-aminomethyl)phenol to give 4-(2',4'-dimethoxyphenyl-Fmoc-aminomethyl)phenoxymethyl-copoly(styrene-divinylbenzene)], an ether also named herein for convenience, Rink amide resin.

Initial efforts to develop a combinatorial approach to explore modified sultams were influenced by Ellman's solid-phase methods wherein the polymer linker arm is removed, leaving a molecule unmodified at the point of former attachment to the linker arm. These methods that were based on a germanium linkage to ring A of the sultam seemed especially amenable to sultam synthesis. However, that method was determined not to be satisfactory. Unlike the Ellman's solid-phase method wherein the polymer linker arm is removed, a method was developed in accordance with the invention wherein the nitrogen atom of the sultams provides a linkage to the resin throughout the reaction steps until its removal concurrently with closure of ring B at the end of the synthesis. The method proved to be highly satisfactory.

Automation of the method of the invention can be carried out, for example, with a commercial automated system such as an AccuTag-100 instrument and SMART microreactors that are encoded, radiofrequency-labeled containers manufactured by IRORI Quantum Microchemistry, San Diego, Calif. Each microreactor carries a radio-frequency chip that records the history of the specific reaction summary for the bead. Separation and identification can be carried out with a bar-code reader.

The compounds of the invention, and their intermediates, are synthesized by the following general procedure. The general scheme and the compounds involved in the synthesis are shown in FIG. 1.

The preparation of Compounds III and IV comprises the following reaction steps. The arylsulfonamide resin I (FIG. 1) is reacted with an excess of alkyl lithium, preferably with an aprotic ethereal solvent (such as tetrahydrofuran) that is distilled from a suitable drying agent (such as sodium) since allyl lithium compounds are known to react violently with protic solvents, in particular, water. Atmospheric moisture should be excluded. The reaction with the alkyl lithium is preferably conducted in an inert gas atmosphere, such as dry nitrogen or argon.

Thereafter, addition of an excess of alkyl lithium to the arylsulfonamide resin results in deprotonation of the sulfonamide nitrogen and lithiation of the ortho-position of the sulfonamide aromatic ring. Since these are exothermic processes, cooling of the reaction mixture to about −78° C. before slow (dropwise) alkyl lithium addition is preferred.

The deprotonated and lithiated arylsulfonamide resin has two types of nucleophilic sites that can potentially attack the carbonyl group of an aldehyde or a ketone II. As a consequence, addition of an excess of an aromatic aldehyde or ketone II, to the deprotonated and lithiated arylsulfonamide resin is believed to result in the formation of a mixture of mono- and bisalkylated sulfonamide resins III and IV.

Figure 5:
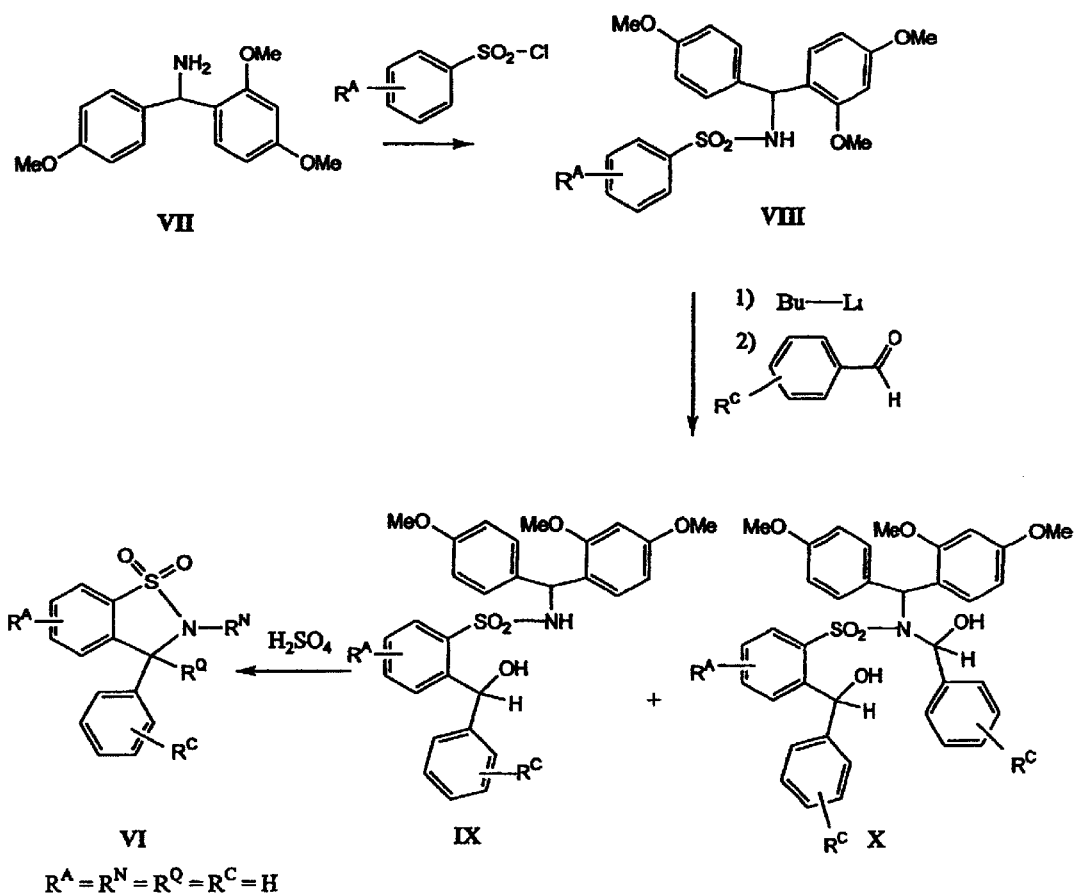
FIG. 5 shows an illustration of a model study using components of the Rink amide resin to develop essential chemistry for the solid-phase approach.
Figure 6:
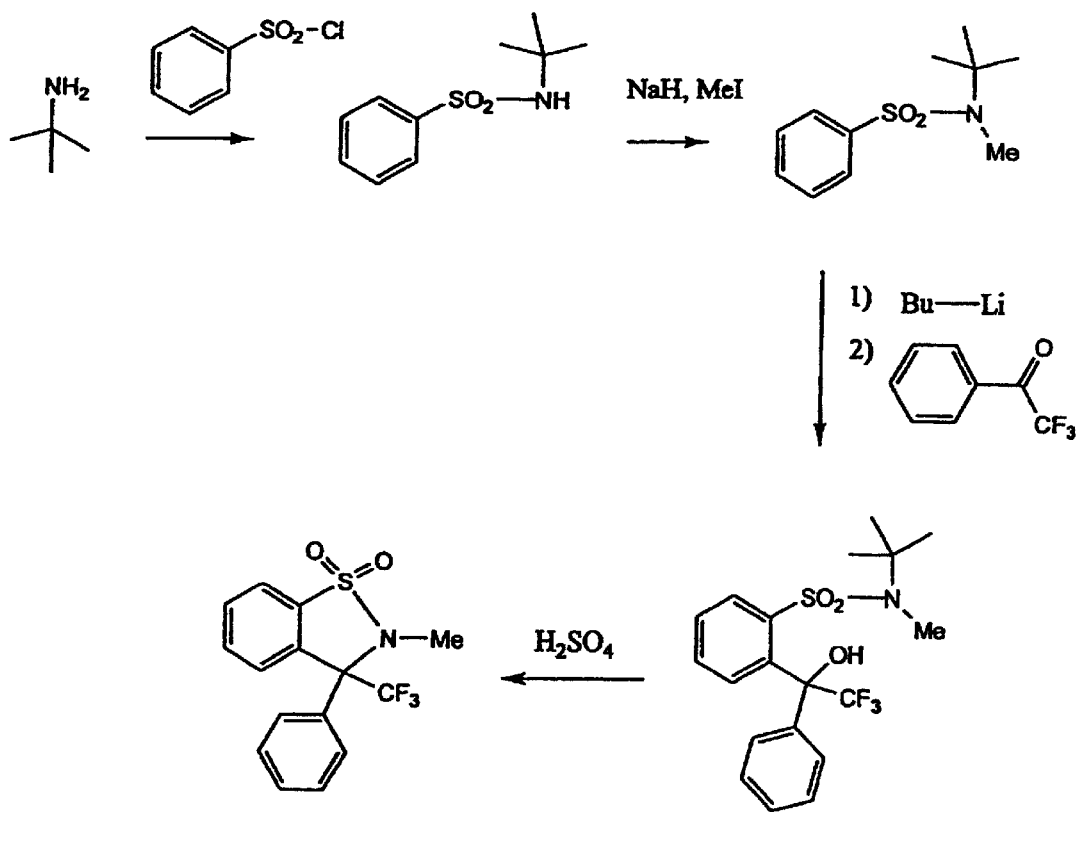
FIG. 6 shows a scheme for study of a solution phase model of the process in conjunction with the development of the solid-phase method to prepare a 3-$CF_3$-substituted sultam.

The formation of compounds III and IV is illustrated in the discussion of the solution-phase model studies carried out in the conjunction with the invention and described further below. The model reaction involved replacing the Rink amine polymer with [(2,4-dimethoxyphenyl)-(4-methoxyphenyl)]methylamine (VII, FIG. 5), which simulates the reactivity of the Rink amine resin or the reactivity of a Rink amine resin equivalent.

Upon alkylation with the aldehyde or ketone, the resin can be washed with an alcohol or other solvent to remove any excess of the aldehyde or ketone. The resin can then be treated to remove the excess solvent, preferably at reduced pressure and ambient temperature.

The alkyl lithium "Li-Alk" which are selected for the reaction with the aryl sufonamide resin is preferably a lower alkyl lithium where the alkyl can be linear or branched of 1 to 6 carbons, like methyl, propyl, isopropyl, isobutyl, or butyl. Since the selection of the aromatic aldehyde or ketone determines the nature of Ring C and its substituents $R^C$ as well as the substituent $R^Q$, a great variety of such reactants are available. Ring C can be an aromatic ring like phenyl, furyl; preferably it is phenyl.

Preferably, Compound II is an aldehyde wherein $R^C$ is hydrogen; alkyl- or alkenyl-(with two or three double bonds), having preferably 1–6 carbon atoms, more preferably 1–4 carbon atoms, linear or branched, alkenyl like ethenyl propenyl, butenyl, isopropenyl, etc.; alkyl like methyl, butyl, isobutyl, propyl, isopentyl; halogen like chlorine, bromine or fluorine; hydroxyl; alkoxy like methoxy; or acylamido like acetamido. $R^Q$ is preferably hydrogen, i.e., an aldehyde, for greater reactivity. When in the synthesis, Compound II is a ketone, $R^Q$ can be alkyl or alkenyl as defined above, preferably methyl; substituted alkyl such as $CCl_3$, $CF_3$ and others; aryl-alkyl, heteroaryl, aryl, or polycyclic, like bicyclic. The heteroatom can be nitrogen, oxygen or sulfur.

Figure 3:
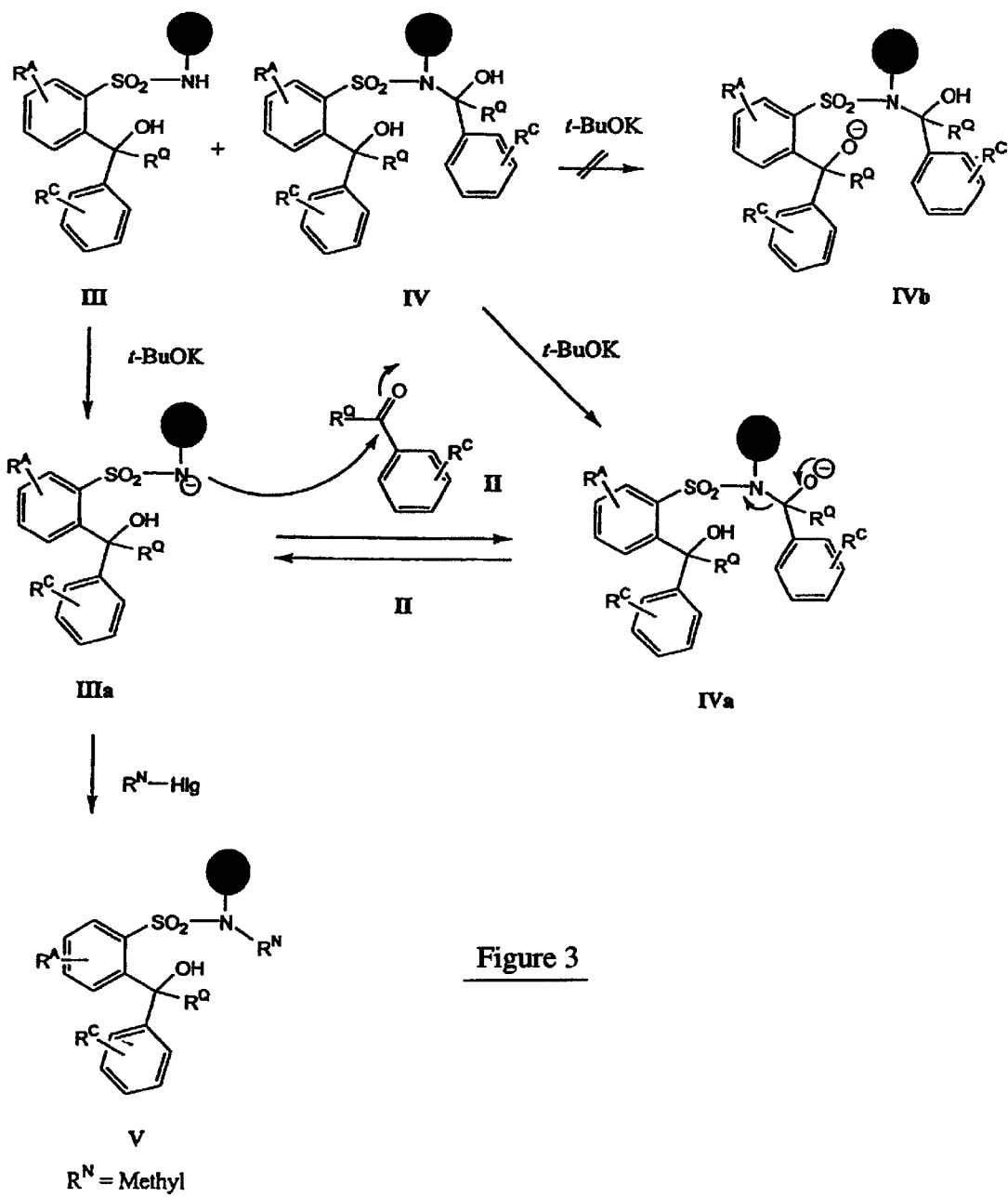
FIG. 3 shows the formation of Compounds IIIa and IVa in the general scheme of the synthesis.
Figure 4:
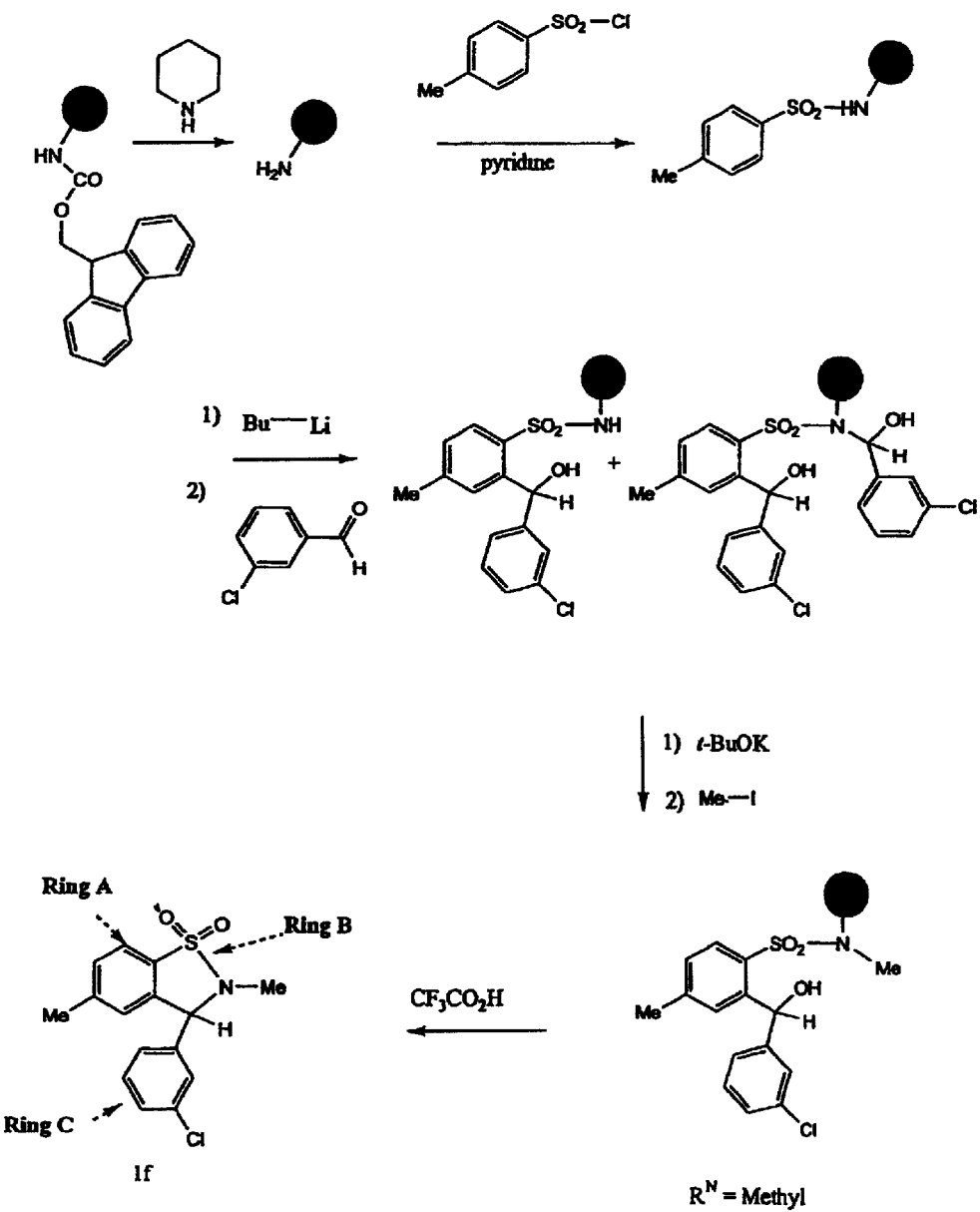
FIG. 4 shows the preparation of a sultam wherein $R^N$ is alkyl.

The preparation of the sulfonamide resin V comprises the following reaction steps. The monoalkylated III and bisalkylated IV sulfonamide resin conjugates have several deprotonation sites as illustrated in FIG. 3. As strong sterically hindered base such as potassium tert-butoxide in a dry ethereal solvent (such as dioxane or tetrahydrofuran) removes a proton from the nitrogen of III to form IIIa. This base also removes the more acidic proton from the N-benzylic alcohol of IV in preference to the proton of the C-benzylic alcohol of IV to form IVa, but not IVb. Reversible addition-elimination of the aromatic aldehyde or ketone II establishes the equilibrium between IIIa and IVa.

The reaction is drawn to the near-exclusive formation of the tertiary sulfonamide resin V (FIGS. 1 and 3) by addition of a 100 to 200-fold excess, preferably 150-fold excess, of an N-alkylating reagent such as iodomethane, which alkylates the nitrogen of IIIa, thus removing IIIa from the equilibrium and providing the substituent $R^N$ on the nitrogen of the target sultams V.

The duration of the reaction can be varied from 10 to 48 hours with 16–24 hours being the preferred duration. The reaction is preferably carried out with gentle agitation of the reaction mixture to minimize breakup of the resin, or with nitrogen stirring (nitrogen gas bubbling through the mixture).

The N-alkylating reagent is preferably iodomethane or any halomethane, methanesulfonate or dimethyl sulfate. With other alkyl reagents like iodoethane and higher alkyl alkylating reagents, the yields of the desired product are not satisfactory due to competing elimination reactions on the reagent themselves.

Upon N-alkylation, the resulting tertiary sulfonamide resin V is washed with solvent to remove unreacted starting materials (such as II or alkyl halide), by-products of the reaction, such as tert-butanol from potassium tert-butoxide, or potassium iodide from methyl iodide or potassium tert-butoxide. Both polar solvents (such as methanol) and apolar solvents (such as dichloromethane) are used for best results. The use of volatile solvents (such as listed above) is preferred, since the excess solvents can be removed from the tertiary sulfonamide resin V under reduced pressure at ambient temperature.

The preparation of target compound VI (FIG. 1) comprises the following reaction steps. The N-alkylated tertiary sulfonamide resin V has two types of easily cleaved carbon-heteroatom bonds. One is the bond linking the nitrogen of the sulfonamide ring to the benzylic carbon of the resin; the other is the carbon-oxygen bond of the benzyl alcohol fragment. These bonds are cleaved upon treatment of V with a strong protic acid, such as trifluoroacetic acid (TFA) or other strong organic acid or strong mineral acid like sulfuric or hydrochloric acid. Addition of protons to oxygen and nitrogen promotes generation of highly stabilized benzylic cations. Cleavage of the bond that links the nitrogen to the resin renders the nitrogen sufficiently active to perform the 5-membered ring closure. Conversely, cleavage of the bond that links the oxygen to the benzylic carbon promotes the 5-membered closure of ring B, which promotes in its turn, the cleavage of the nitrogen-resin bond. In this manner, ring closure to the sultam is completed essentially concurrently with cleavage of the resin from the rest of the molecule.

Once the target compound VI is cleaved from the resin, it can be easily separated from the solid phase (the decomposed resin) by washing the resin with an alcohol (such as methanol) or another solvent that displays selective dissolving capacity for the target sultam, but not for the decomposed resin. The target VI sultam can then be treated to remove the solvent under reduced pressure. Gas or liquid chromatography can be used to monitor the purity of the product.

Target compound VI is obtained as a racemate, which is comprised of a pair of enantiomers. To separate the enantiomers, several procedures can be used. The enantiomers can be separated on a chiral chromatography column; or an enantiomerically pure chiral moiety can be appended, thus generating diastereomers, which are then separated on an achiral (non-chiral) column, removing the chiral moiety upon separation, thus generating separate enantiomers. Suitable methods are known. See, for example, ref 22, Chapter 7, cited herein above.

Figure 2:
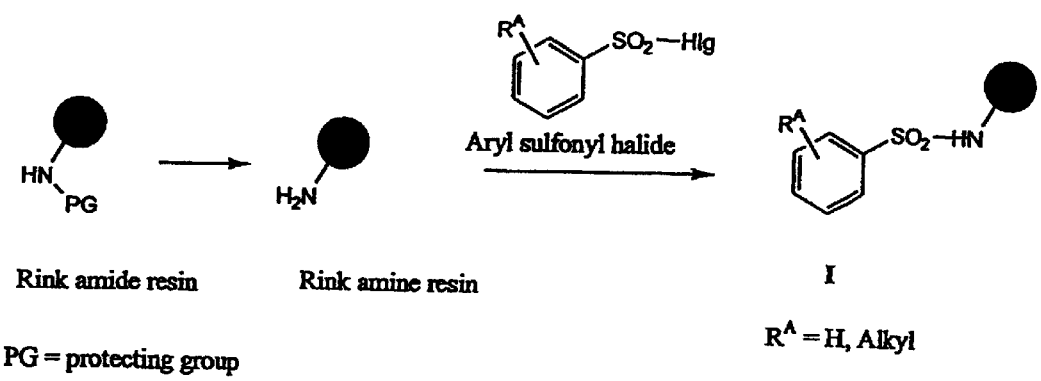
FIG. 2 shows the preparation of the sulfonamide resin.

In the event that a resin-bound secondary sulfonamide of the structure I is not readily available, it can be obtained from a Rink amine resin or from similar resins. Preferably, the Rink amine resin is freshly prepared by removing protecting groups from the nitrogen termini of a Rink amide resin (FIG. 2) by methods described in the literature. Removal of the protecting groups (such as fluorenyl methoxycarbonyl) and formation of the Rink amine resin can be monitored by high-resolution magic-angle nuclear magnetic resonance spectroscopy of the resin by methods described in ref. 13.

The resin is then treated with an excess (20–40 molar equivalents, preferably 30 molar equivalents) of aryl sulfonyl halide (FIG. 2), preferably an aryl sulfonyl chloride in the presence of base (preferably a non-nucleophilic bulky nitrogen base) in an aprotic solvent. The solvent, either taken alone or in conjunction with the organic base, should preferably display a selective affinity to the resin, i.e., swell the resin, and a dissolving capacity for aryl sulfonyl halides. Tetrahydrofuran is the preferred solvent.

The secondary amine formation can be carried out as described in the prior art. It is preferably performed with agitation of the reaction mixture. The temperature range can vary from −10 to 50° C., with the 17–26° C. temperature range being preferred. The duration of the reaction can be varied from 1 to 24 hours, with 3–6 hours being the preferred duration. The sulfonated resin can be washed with an alcohol and other organic solvents to remove the excess of the aryl sulfonyl halide, as well as the halide salt of nitrogen base and other contaminants. Suitable solvents include polar aprotic solvents such as N,N-dimethylformamide and ethereal solvents such as diethyl ether. The sulfonated resin can then be treated to remove the excess solvent, preferably at reduced pressure and room temperature. The formation of the sulfonamide resin can be monitored by high-resolution magic-angle nuclear magnetic resonance spectroscopy of the resin (ref. 13).

The synthesis of the invention lends itself to modification for particular substituents on the rings. In the sultams when $R^N$ is hydrogen, the synthesis of target compound VI is performed as follows. Sultam VI (FIG. 1) is synthesized with the omission of the addition of a strong sterically hindered base and of an alkyl halide such as iodomethane to the mixture of monoalkylated III and bisalkylated IV sulfonamide resin conjugates, which yield a sultam wherein $R^N$ is hydrogen.

Generation of sultam VI is possible due to the interconversion of IV into III upon the addition of a protic acid as described above. When III is subjected to acidic conditions, it undergoes ring closure, as well as cleavage from the resin to yield target sultam VI. In that step, the reactivity of III is similar to that of V, apparently because of their structural similarity.

Model Reaction With Sultam Wherein All "R" Substituents Are Hydrogen

In the development of the invention, it became of interest to confirm the mechanistic rationale of the invention in a synthesis that did not use a solid support and to provide data on the structures of the intermediates in the solid-phase synthesis. To this end, a low molecular weight compound (2,4-dimethoxyphenyl)-(4-methoxyphenyl)methylamine VII (FIG. 5), was selected which mimics the chemical reactivity of the Rink amine resin, since it is structurally similar to a fragment of the Rink amine resin shown in FIG. 2. Addition of benzenesulfonyl chloride in presence of a base such as triethylamine results in the formation of a sulfonamide VIII (FIG. 5), which is a structural analog of the arylsulfonamide resin I, FIG. 1. Deprotonation and lithiation of the sulfonamide VIII with subsequent addition of benzaldehyde results in formation of mono- and bisalkylated sulfonamides IX and X. This result allowed one to postulate the formation of the mono- and bisalkylated sulfonamide resins III and IV (FIG. 1), which are resin-linked structural analogs of compounds IX and X.

Addition of an alkyl halide can be omitted, as discussed above when it is desired to obtain sultams VI, wherein $R^N$ is hydrogen. Treatment of the mixture of IX and X with a protic acid as discussed above causes X to split off the benzaldehyde fragment to form the monoalkylated sulfonamide IX, which, in its turn, undergoes ring closure, as well as cleavage from the residues of Compound VII to yield target sultam VI, wherein the substituents $R^A$, $R^N$, $R^Q$, and $R^C$ are all hydrogens.

The substituents on Ring C are determined by the substituents on the aldehyde or the ketone reactant, as they were in the solid-phase synthesis of the sultams described above. Other than a phenyl ring, ring C can be furyl when 2-furaldehyde is the reactant. Likewise, the nature of the sulfonyl chloride selected, in this illustration, benzenesulfonyl chloride, determines the nature of substituent $R^A$. When a sulfonyl chloride is selected which is an aryl sulfonyl other than phenyl, like 4-pyridyl, the compounding VI is obtained wherein ring A in 4-pyridyl.

As is shown, the reaction with a compound which mimics the role of the Rink resin or its equivalent provides an alternative to the solid-phase synthesis of the sultams of the invention with variations in the substituents of the sultams to yield target sultams VI, by selection of the corresponding reactants.

Typical compounds of the invention with their respective substituents are shown in Table I.

TABLE I

| Typical Sultams of the Invention | | | | |
|---|---|---|---|---|
| Compound | $R^A$ | $R^N$ | $R^Q$ | $R^C$ |
| 1 | H | Me | H | H |
| 2 | (S)-enantiomer of 1. | | | |
| 3 | (R)-enantiomer of 1. | | | |
| 4 | H | Me | H | 3-Me |
| 5 | (S)-enantiomer of 4. | | | |
| 6 | H | Me | H | 3-F |
| 7 | (S)-enantiomer of 6. | | | |
| 8 | H | Me | H | 3-Cl |
| 9 | (S)-enantiomer of 8. | | | |
| 10 | (R)-enantiomer of 8. | | | |
| 11 | H | Me | H | 3-Br |

TABLE I-continued

Typical Sultams of the Invention

| Compound | $R^A$ | $R^N$ | $R^Q$ | $R^C$ |
|---|---|---|---|---|
| 12 | (S)-enantiomer of 11. | | | |
| 12a | H | Me | H | 2-I |
| 13 | H | Me | H | 3-I |
| 14 | H | Me | H | 3-$CF_3$ |
| 16 | H | Me | H | 2-Cl |
| 17 | H | Me | H | 2-Me |
| 18 | H | Me | H | 4-Me |
| 19 | (R)-enantiomer of 18. | | | |
| 21a | H | Me | H | 2-Br |
| 22a | H | Me | H | 2-F |
| 23 | H | Me | H | 4-OMe |
| 24 | (S)-enantiomer of 23. | | | |
| 26 | H | Me | H | $NHCOCH_3$ |
| 27 | H | Me | H | 4-F |
| 28 | H | Me | H | 4-Cl |
| 29 | H | Me | H | 4-Br |
| 30 | H | Me | H | 4-Ph |
| 31 | H | Me | H | 2-Me, 5-Me |
| 32 | H | Me | H | 2-Cl, 3-Cl |
| 33 | H | Me | H | 2-Cl, 6-Cl |
| 34 | H | Me | H | $C_6F_5$ |
| 35 | H | H | H | H |
| 36 | H | H | H | 3-Cl |
| 37 | H | Et | H | 3-Cl |
| 38 | H | Bu | H | 3-Cl |
| 39 | H | t-Bu | H | 3-Cl |
| 41 | H | 2-Pr | H | H |
| 42 | H | Me | Me | H |
| 43 | H | Me | Me | 2-Cl |
| 44 | H | Me | Me | 3-Cl |
| 46 | H | Me | CF3 | H |
| 47 | 5-Me | Me | H | H |
| 48 | 5-Me | Me | H | 3-Cl |
| 49 | 5-Me | Me | H | 4-F |
| 50 | 5-Me | Me | H | 2-furyl |
| 52 | 5-Me | Me | H | 4-OMe |
| 53 | 5-Me | Me | Me | H |
| 54 | 5-Cl | Me | H | H |
| 55 | 5-Cl | Et | H | H |
| 56 | 5-Cl | Pr | H | H |
| 57 | H | Me | H | 3-Et |
| 58 | H | Me | H | 3-vinyl |

Other compounds of the invention can be synthesized using other reactants that will yield the corresponding substituents on the target sultams.

The Solid Supports for the Reaction

The synthesis of the invention can be carried out using modifications of solid supports for the reaction and/or alternatives for the Rink amine resin. The Rink amine resin is a synthetic resin frequently used as a support for the synthesis of peptides and peptide amides on solid phase in accordance with the known general principles of the Merrifield synthesis. The synthetic resin consists of a skeletal structure of polystyrene that has been cross-linked with up to 5 mole % of divinylbenzene and has been substituted on the benzene rings of its skeletal structure.

In the process of the invention, it is not essential that a Rink amine resin be used. A molecule which has an equivalent structure (or one that does not have an equivalent structure) and yet performs the same or equivalent function as the Rink amine resin in the series of reactions set forth in the synthesis of the target compounds, will be quite satisfactory. Such a molecule can comprise a synthetic resin other than the divinylbenzene cross-linked polystyrene resin as the Rink amine resin, such as another synthetic resin that would provide the solid support for the reactions and facilitate the chemical process.

There are a variety of commercially available resins, from which suitable candidates can be selected. For instance, the molecule may provide a protected amine group and allow the separation of the nitrogen from the resin and allow the 5-membered ring closure by forming a stable carbocation center when treated with strong acids. For example, suitable resins are the modified Rink resins Rink Amide AM resin and Rink Amide MBHA resin, as well as the Sieber Amide. It is also feasible to start with resins with a free amino group. The amino-4-(methoxyphenyl)methyl polystyrene resin and MBHA resin.HCl are good candidates which form stable intermediates in the reaction as mentioned above. Certain resins are not preferred in this application, such as the aminomethylated polystyrene resin, which are not as suitable due to their less stable carbocations when the resin is treated with strong organic or inorganic acids, which tends to hinder the cleavage and closure of the structure into ring B. Various proposals for different resins are also found in the literature.

Suitable resins which can be used in the synthesis area available commercially such as from Calbiochem-Novabiochem Corp. Typical are: the Rink Amide AM resin, Rink Amide MBHA resin, amino-(4-methoxyphenyl)methyl polystyrene, MBHA resin.HCl and the Sieber Amide resin.

The invention also relates to the salts of the basic or acid derivatives of the compounds of the invention, for instance, those which have an acidic group or a sufficiently basic nitrogen. Particularly preferred are the pharmaceutically acceptable salts of the instant compounds which retain biological activity. Acid addition or cationic salts of the compounds of the invention are prepared in a standard manner.

In brief, an excess of an acid, such as hydrochloric, hydrobromic, sulfuric, phosphoric, formic, acetic, maleic, or succinic, is added to the parent compound. In particular, the acetate salt form can be especially useful. In addition, certain of the compounds may form inner salts or zwitterions which may be acceptable. Cationic salts are prepared by treating the parent compound with an excess of an alkylating reagent, such as hydroxide, carbonate or alkoxide containing the appropriate cation. Cations such as $Na^+$, $K^+$, $Ca^{2+}$, and $NH_4^+$ are examples of cations present in pharmaceutically acceptable salts.

The following examples are illustrative of the synthesis and of the sultams of the invention, and they are not intended to limit the invention in any way.

EXAMPLE 1

The synthesis of sultams wherein $R^Q$ is hydrogen proceeds as follows. 9-Fluorenylmethoxycarbonyl-protected Rink amide resin (0.45 g having a loading of 0.47 mmol/g, 0.21 mmol) was treated with a mixture of piperidine (5 mL), toluene (5 mL) and N,N-dimethylformamide (DMF, 5 mL). After 1.5 h shaking on a mechanical shaker (Burell "Wrist Action" model 15), the resin was washed with Do (two portions of 10 mL) and dichloromethane (two portions of 10 mL). Pyridine (6 mL), dichloromethane (20 mL) and p-toluenesulfonyl chloride (1.15 g, 6.03 mmol) were added to the deprotected resin, and the reaction flask was shaken for 4.5 hours at room temperature. The resin was then filtered and washed with methanol (10 mL), DMF (two portions of 10 mL) and tetrahydrofuran (two portions of 2 mL). The sulfonated resin was dried in vacuum (0.1 torr) for 1 hour at room temperature.

To the dried sulfonamide resin obtained as described above, dry tetrahydrofuran was added (20 mL, freshly distilled from Na-benzophenone ketyl), and the flask was cooled by immersion into liquid nitrogen bath for about 20 s with shaking. Butyllithium (1 mL of a commercially available 10.0 M solution in hexanes, 10 mmol) was then added dropwise via syringe with shaking of the reaction flask. After the addition was complete, the resin color changed from pale yellow to brownish black. m-Chlorobenzaldehyde (1.2 ml, 10.6 mmol) was then added dropwise until the resin color returned to pale yellow, while the solution color turned to brown-red. The flask was shaken for additional 10 minutes; then methanol was added. After the resin had settled, the brown solution was removed with a pipet, and the resin was washed with methanol (two portions of 10 mL) and tetrahydrofuran (two portions of 10 mL). The pale-yellow resin was dried in vacuum (0.1 torr) for 1 hour at room temperature.

Tetrahydrofuran (15 mL) and potassium tert-butoxide (2 mL of a 1 M solution in tetrahydrofuran, 2 mmol) were added to the resin with hand shaking. After the resin color changed to deep brown, iodomethane (2 mL, 32 mmol) was added, and the flask was shaken for 20 h. Methanol was then added to dissolve the precipitate. The resin was washed by methanol (two portions of 10 mL) and dichloromethane (two portions of 10 mL) and dried in vacuum for 1 h at room temperature to yield 0.4562 g of the N-methylated tertiary sulfonamide resin.

To a portion of the N-methylated tertiary sulfonamide resin (0.0424 g) 4 mL of trifluoroacetic acid solution in dichloromethane (25% by volume) was added. The resin color instantly changed from yellow to blood red. The reaction mixture was shaken for 19 h at ambient temperature. Methanol was then added and the red resin was filtered off The methanolic filtrate was concentrated to give the target sultam VI wherein $R^Q$ if necessary is hydrogen as a dark-brown syrup in a 88% overall yield (5.3 mg). The purity of the product was confirmed by GC-MS (gas chromatography/mass spectrometry).

EXAMPLES 2–53

In the following examples the substituents $R^A$, $R^N$, $R^Q$ and $R^C$ are as shown on sultam VI, with the reactants listed under each substituents. The conditions are in general as shown in Example 1.

TABLE II

Illustrative Sultams of the Invention
Substituents $R^Q$ and $R^C$ originate from the same reactant, either an aldehyde or a ketone.

| Compound | $R^A$ | $R^N$ | $R^Q$ | $R^C$ |
|---|---|---|---|---|
| 1 | H benzenesulfonyl halide | Me MeI | H benzaldehyde | H |
| 2 | (S)-enantiomer of 1. | | | |
| 3 | (R)-enantiomer of 1. | | | |
| 4 | H benzenesulfonyl halide | Me MeI | H m-methyl-benzaldehyde | 3-Me |
| 5 | (S)-enantiomer of 4. | | | |
| 6 | H benzenesulfonyl halide | Me MeI | H m-fluoro-benzaldehyde | 3-F |
| 7 | (S)-enantiomer of 6. | | | |
| 8 | H benzenesulfonyl halide | Me MeI | H m-chloro-benzaldehyde | 3-Cl |

TABLE II-continued

Illustrative Sultams of the Invention
Substituents $R^Q$ and $R^C$ originate from the same reactant, either an aldehyde or a ketone.

| Compound | $R^A$ | $R^N$ | $R^Q$ | $R^C$ |
|---|---|---|---|---|
| 9 | (S)-enantiomer of 8. | | | |
| 10 | (R)-enantiomer of 8. | | | |
| 11 | H benzenesulfonyl halide | Me MeI | H m-bromo-benzaldehyde | 3-Br |
| 12 | (S)-enantiomer of 11. | | | |
| 12a | H benzenesulfonyl halide | Me MeI | H o-iodo-benzaldehyde | 2-I |
| 13 | H benzenesulfonyl halide | Me MeI | H m-iodo-benzaldehyde | 3-I |
| 14 | H benzenesulfonyl halide | Me MeI | H m-(tri-fluoromethyl) benzaldehyde | 3-CF3 |
| 16 | H benzenesulfonyl halide | Me MeI | H o-chloro-benzaldehyde | 2-Cl |
| 17 | H benzenesulfonyl halide | Me MeI | H o-methyl-benzaldehyde | 2-Me |
| 18 | H benzenesulfonyl halide | Me MeI | H p-methyl-benzaldehyde | 4-Me |
| 19 | (R)-enantiomer of 18. | | | |
| 21a | H benzenesulfonyl halide | Me MeI | H o-bromo-benzaldehyde | 2-Br |
| 22a | H benzenesulfonyl halide | Me MeI | H o-fluoro-benzaldehyde | 2-F |
| 23 | H benzenesulfonyl halide | Me MeI | H p-methoxy-benzaldehyde | 4-OMe |
| 24 | (R)-enantiomer of 24. | | | |
| 26 | H benzenesulfonyl halide | Me MeI | 4-acetamido-benzaldehyde | NHCOCH3 |
| 27 | H benzenesulfonyl halide | Me MeI | H p-fluoro-benzaldehyde | 4-F |
| 28 | H benzenesulfonyl halide | Me MeI | H p-chloro-benzaldehyde | 4-Cl |
| 29 | H benzenesulfonyl halide | Me MeI | H p-bromo-benzaldehyde | 4-Br |
| 30 | H benzenesulfonyl halide | Me MeI | H 4-phenyl-benzaldehyde | 4-Ph |
| 31 | H benzenesulfonyl halide | Me MeI | 2,5-dimethyl-benzaldehyde | 2-Me, 5-Me |
| 32 | H benzenesulfonyl halide | Me MeI | H 2,3-dichloro-benzaldehyde | 2-Cl, 3-Cl |
| 33 | H benzenesulfonyl halide | Me MeI | H 2,6-dichloro-benzaldehyde | 2-Cl, 6-Cl |
| 34 | H benzenesulfonyl halide | Me MeI | H pentafluoro-benzaldehyde | F5 |
| 35 | H benzenesulfonyl halide | H no alkyl halide added | H benzaldehyde | H |

TABLE II-continued

Illustrative Sultams of the Invention
Substituents $R^Q$ and $R^C$ originate from the same reactant,
either an aldehyde or a ketone.

| Compound | $R^A$ | $R^N$ | $R^Q$ | $R^C$ |
|---|---|---|---|---|
| 36 | H benzenesulfonyl halide | H no alkyl halide added | H m-chlorobenzaldehyde | 3-Cl |
| 37 | H benzenesulfonyl halide | Et ethyl iodide | H m-chlorobenzaldehyde | 3-Cl |
| 38 | H benzenesulfonyl halide | Bu n-butyl iodide | H m-chlorobenzaldehyde | 3-Cl |
| 39 | H benzenesulfonyl halide | t-Bu t-butyl iodide | H m-chlorobenzaldehyde | 3-Cl |
| 41 | H benzenesulfonyl halide | Isopropyl isopropyl iodide | H benzaldehyde | H |
| 42 | H benzenesulfonyl halide | Me MeI | Me acetophenone | H |
| 43 | H benzenesulfonyl halide | Me MeI | Me o-chlorophenyl methyl ketone | 2-Cl |
| 44 | H benzenesulfonyl halide | Me MeI | Me m-chlorophenyl methyl ketone | 3-Cl |
| 46 | H benzenesulfonyl halide | Me MeI | CF3 trifluoromethyl phenyl ketone | H |
| 47 | 5-Me p-toluenesulfonyl halide | Me MeI | H benzaldehyde | H |
| 48 | 5-Me p-toluenesulfonyl halide | Me MeI | H m-chlorobenzaldehyde | 3-Cl |
| 49 | 5-Me p-toluenesulfonyl halide | Me MeI | H p-fluorobenzaldehyde | 4-F |
| 50 | 5-Me p-toluenesulfonyl halide | Me MeI | H 2-furaldehyde | H[a] |
| 52 | 5-Me p-toluenesulfonyl halide | Me MeI | H p-methoxybenzaldehyde | 4-OMe |
| 53 | 5-Me p-toluenesulfonyl halide | Me MeI | Me acetophenone | H |
| 54 | 5-Cl p-chlorobenzenesulfonyl halide | Me MeI | H benzaldehyde | H |
| 55 | 5-Cl p-chlorobenzenesulfonyl halide | Et ethyl iodide | H benzaldehyde | H |
| 56 | 5-Cl p-chlorobenzenesulfonyl halide | Propyl propyl iodide | H benzaldehyde | H |
| 57 | H benzenesulfonyl halide | Me MeI | H m-ethylbenzaldehyde | 3-Et |
| 58 | H benzenesulfonyl halide | Me MeI | H m-ethenylbenzaldehyde | 3-vinyl |

[a] The ring is furyl.

Combinatorial Synthesis and Automation

The solid-phase combinatorial synthesis of the sultams of the invention lends itself to automation for generating large libraries of sultams. The process can be carried out in a combinatorial (pool and split) manner, where a large number of synthesized compounds are screened for desired activities, such as anti-HIV activity in this application. The active compounds can be identified by their molecular tags.

In order to make each compound in the library recognizable, certain methods have been developed, such as chemical tagging. Tagging molecules, such as dyes and fluorescent compounds, are attached to the beads (solid support) by chemical methods. By identifying the code from the tags, the compounds of interest can be recognized. An alternative is the radio-frequency (RF) encoding system. Each microreactor carries a radio-frequency chip that records the structure and the history of the specific reaction summary for the bead. Each component of the library has a unique combined code, which can be decoded by a bar-code reader. This method is compatible with virtually all synthetic methods, since no chemical reactions are necessary in the encoding and retrieval process.

In this manner, efficient and automated solid-phase synthesis of the sultams of the invention is achieved. Commercial automated systems are available, such as AccuTag-100 instrument and SMART microreactors (MicroKans and MicroTubes) that are encoded, radiofrequency-labeled containers manufactured by IRORI Quantum Microchemistry, San Diego, Calif.

Identification of the Optical Activity of the Sultams

To facilitate identification of the optical activity of the sultams of the invention, the chirality is determined as follows: When the optical rotation is measured in a polarimeter, the sign of rotation can be either positive or negative at a given wavelength of light. An optical rotation of 0 (zero) is also possible, in which case one must examine the rotation at another wavelength. The expression (+) and (−) indicates the physical properties of this compound, but tells nothing about the absolute stereochemistry. A pair of enantiomers have the same magnitude of optical rotation (°) but different signs. To define a chiral center with exact spacial relationship, all four substituents are prioritized by the atomic number of the first atom(s) of the substituents from the chiral center. This is termed the Cahn-Ingold-Prelog system; see ref 22, Chapter 7. If two or more atoms are of the same number, the next atom in the substituents are compared, and so on. The group with the least priority is set behind an imaginary plane and the other three are arranged on the plane, without changing their relative positions. A circle is drawn from the most prioritized to the second, then to the third prioritized group. If the circle is clockwise, the absolute configuration is an "R" configuration; if the circle is counterclockwise, it is an "S" configuration. A pair of enantiomers (with one or more chiral centers) have opposite sign for (R) and (S) at all chiral centers. A pair of diastereomers are isomers in which not all chiral centers are opposite. The (+)(−) signs are not by definition related to the absolute configuration (R)(S). In this text, however, the (+) isomer was determined to be always the (S) isomer, except for substituents at C-2 for the ring C phenyl group that have a priority greater than a carbon atom, in which case the priority is (R).

Separation of Enantiomers

Whenever a racemic mixture of a compound of the invention is obtained and if it is desired to separate into the pure enantiomers, the following of several procedures can be followed. The resulting racemic sultams can be separated by one or more known chemical or other methods. In chiral column chromatography, for instance, using a Chiralcel OD HPLC column, one enantiomer can be eluted out of the column faster than the other, thus allowing for the separation. Otherwise, the two enantiomers can be derivatized to diastereomers by reacting with optically active reagents whose groups can later be removed. The two diastereomers can be separated by their different physical and chemical properties, for example, distillation (if the compounds are volatile), recrystallization (if at least one of the compounds can be crystallized), and chiral or achiral column chromatography. After the separation, the chiral auxiliaries can be cleaved and the two enantiomeric sultams are obtained. Such methods are known in the art. See ref 22, Chapter 7. A highly suitable method to prepare the target enantiomer from a racemic mixture of sultam involves removing a protecting group (PG) (such as methyl or acyl) from a substituent (such as methoxy or an N-acyl group) linked to the racemic sultam by reaction with a protic or Lewis acid (such as a strong inorganic acid like hydrochloric acid or boron tribromide), thus obtaining a racemic mixture (50/50) of the sultams with a hydroxy group on the C-ring or a free amino. Thereafter, the hydroxy or the free amino group of the racemic sultam is derivatized with a enantiomerically pure electrophilic chiral reagent (such as (−)-camphanic acid chloride), thereby obtaining a mixture of two diastereomeric sultam derivatives, which are separated by chromatography. The chiral moiety is then removed from the separated diastereomeric sultam derivatives by treating them with a hetronucleophilic reagent (such as ammonia in methanol), thereby obtaining the enantiomers pure or substantially pure, i.e., over 90% by weight, preferably over 95% by weight and most preferably over 99% by weight of pure sultam. When anti-HIV activity is desired, the (+)-S enantiomers are preferred (except as described herein where the Calin-Ingold-Prelog priorities are reversed, the (+)-R enantiomers are preferred).

The biological compositions of the invention are likewise preferably, especially when anti-HIV activity is desired, substantially free of the (+)-R enantiomer with the exception noted above.

The method of treating, alleviating or preventing a viral infection comprises administering the desired enantiomer, substantially free (as described above) of the less desired enantiomer to the mammal, e.g., the human. Preferably, the administration of the selected compound of the invention is performed while avoiding the concomitant undesired activity, if any, and/or the reduction of potency attributable to the less desired enantiomer.

It should be noted that, whereas preferences have been taught herein regarding certain of the enantiomers, especially for anti-HIV potency, when other activities, for instance biological (e.g., in mammals, plants or other) are desired, it is not unlikely that the herein described less desirable enantiomer (for anti-HIV activity) is the more desired enantiomer for such other activity. Methods for obtaining the target enantiomer is described hereinafter. For anti-HIV activity the target enantiomer are the (+)-S enantiomers.

Biological Activities of the Compounds of the Invention

Introduction

In studies in conjunction with the invention, it was found that the anti-HIV activity of the compounds of the invention varied in an unforeseeable manner depending on the nature of the individual substituents, on the size and bulkiness of the substituents, their polarity, the ring on which and at which position the substituent(s) is linked, whether or not the nitrogen is substituted, and by what substituent, whether there is a substituent on the stereogenic center, at C-3; and in what position (ortho-, meta-, or para-) the substituents were linked on the C ring of the sultams. From the data of anti-HIV structure-activity relationships, it was thus observed that both steric and electronic factors played an important role. These studies further suggested that the most active sites for substitutions to be positioned is on the nitrogen of the B ring and the ortho- or meta-position of the C ring. Sultams which are highly preferred are those numbered 57 and 58 identified in Table m hereinbelow, and their respective (+)-(S) enantiomers.

Antiviral/anti-HIV Activity of the Sultams

A primary objective of the invention was to find compounds that exhibit high activity as antiviral, especially anti-HIV activity. Indeed, as described, the sultams of the invention are highly effective in that respect, whether as racemates, or when resolved in their respective (+)-enantiomers. The sultams of the invention have biological activity that make them interesting candidates for biological applications other than (or in addition to) anti-HIV drugs. It is not excluded that they may have fungicidal, insecticidal or the property to control other undesirable microorganisms, which is of interest in agricultural applications. Veterinary applications to control animal infections are also contemplated. The sultams of the invention are especially useful to inhibit the growth or replication of a virus in animals, especially mammals. Examples of mammals include humans, primates, bovines, ovines, porcines, felines, canines, elephantidae, etc. Examples of viruses include but are not limited to HIV-1, HIV-2, herpes simplex virus (types 1 and 2), varicella zoster virus, cytomegalovirus, papilloma vikrus, HTLV-1, HTLV-2, feline leukemia virus, avian sarcoma viruses such as rous sarcoma virus, hepatitis types A–E, influenza virus, measles, mumps and rubella viruses. In a presently preferred use the compounds of the invention are used to treat a human at risk, exposed or infected (i.e., in need of such treatment) with the human immunodeficiency virus, either prophylactically or therapeutically.

The sultams of the invention are accordingly particularly useful in the treatment of infection by the human immuno-deficiency virus and also in the treatment of consequent pathological conditions associated with AIDS. Treating AIDS is defined as including, but not limited to, treating a wide range of states of HIV infection: AIDS, ARC (AIDS related complex), both symptomatic and asymptomatic, and actual or potential exposure to HIV. For example, the sultams of the invention are useful in treating infection by HIV after suspected exposure to HIV by e.g., blood transfusion, exposure to patient blood during surgery, or an accidental hypodermic needle stick.

An advantage to compounds of the invention is that they retain the ability to inhibit HIV RT mutants that are resistant to TIBO and other compounds known to inhibit RT. This is advantageous over the current AIDS drug therapy, where biological resistance tends to develop to nucleoside or non-nucleoside analogues used in the inhibition of RT.

As described herein above, the compounds of the invention are non-nucleoside reverse transcriptase inhibitors (NNRTI), also referred to as "second-site" RT inhibitors. Refs. 27, 28, 29, 30, 31 and 32. The compounds of the invention influence the metabolic pathway by allosteric (noncovalent) regulation. They bind with remarkable affinity to (or fit to or into) the allosteric regulatory site and influence the RT catalytic site; hence the sultams are considered inhibitory modulators specific and binding to the allosteric site. This site is believed to be found on the regulatory subunit of the RT enzyme, which is in communication with the catalytic subunit of the RT through conformational changes. Ref. 33. The preferred sultams of the invention have been found to conform or fit to the regulatory site of the enzyme with an affinity heretofore not yet observed, of an order of magnitude be in the range of $10^{-8}$ to $10^{-9}$ M for inhibition of 80–100% of the enzyme's activity. Other inhibitory allosteric modulators of the RT enzyme, which are substantially equivalent or better than the sultams of the invention, are considered to be within the scope of the present invention.

The sultams of the invention may be assayed for antiviral activity in accordance with published protocols. They include, but are not limited to, cell count, cytopathic effect, dish-macrocytes/macrophages with either HIV-1 or HIV-2. At six or more days post-infection, measurement of particle-associated reverse transcriptase activity and/or p24 antigen levels can be determined (see, for example, Clapham et al. Nature, 337:368–370 (1990) or McDougal et al. *J. Immun. Meth.*, 76:171–183 (1985). In addition, the focal infectivity assay (FIA) can be used to assay the susceptibility of HIV to antiviral agents (see, e.g., Pincus et al., *Bio. Techniques,* 10:336–342 (1991).

Furthermore, the levels of antiviral "activity" of the compounds of the present invention can be rapidly determined in a series of interrelated assays via a semiautomated multiparameter approach as disclosed by Gulakowski et al., *J. Virol. Meth.* 33:87–100 (1991), which is incorporated herein by reference.

The sultams of the invention were tested in accordance with the National Cancer Institute Protocol, Weislow, O. W. et al., *J. Natl. Cancer Inst.,* 81:577–586 (1989), which is incorporated herein by reference. The protocol is also described in U.S. Pat. No. 5,843,990.

The anti-HIV activity of compounds of the invention illustrated by the formula VI shown above, is reported below.

TABLE III

Biolocial Activities of Synthesized Sultams

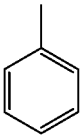

| No. | $R^N$ | $R^O$ | Ring C | $R^A$ | Config. | Opt. Rot. (deg.) | mp (deg. C.) | $EC_{50}$ ($\mu$M) | $IC_{50}$ ($\mu$M) | $TI_{50}$ | Act.[1] |
|---|---|---|---|---|---|---|---|---|---|---|---|
| 1 | Me | H | 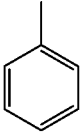 | H | (+/−) | — | — | — | — | — | A |
| 2 | Me | H | 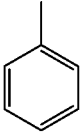 | H | (+)-(S) | 147 | 156–157 | 0.471 | >316 | >674 | A |
| 3 | Me | H | 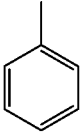 | H | (−)-(R) | −148 | 156–157 | — | >316 | — | I |
| 4 | Me | H | 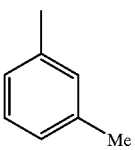 | H | (+/−) | — | 103 | 0.036 | >200 | >556 | A |

TABLE III-continued
Biolocial Activities of Synthesized Sultams
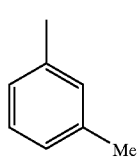
| No. | $R^N$ | $R^O$ | Ring C | $R^A$ | Config. | Opt. Rot. (deg.) | mp (deg. C.) | $EC_{50}$ ($\mu M$) | $IC_{50}$ ($\mu M$) | $TI_{50}$ | Act.[1] |
|---|---|---|---|---|---|---|---|---|---|---|---|
| 5 | Me | H | 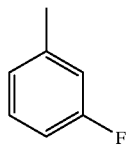 3-Me | H | (+)-(S) | 149 | 154 | 0.037 | >2.0 | >54 | A |
| 6 | Me | H | 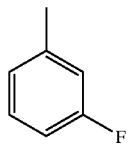 3-F | H | (+/−) | — | 127 | 0.173 | 66.7 | 385 | A |
| 7 | Me | H | 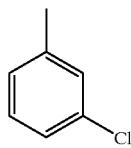 3-F | H | (+)-(S) | | | — | — | — | — |
| 8 | Me | H | 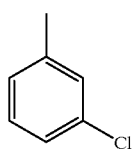 3-Cl | H | (+/−) | — | 133 | 0.38 | 113 | 297 | A |
| 9 | Me | H | 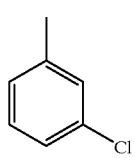 3-Cl | H | (+)-(S) | 166 | 164 | 0.086 | >2 | >31 | A |
| 10 | Me | H | 3-Cl | H | (−)-(R) | −150 | 160 | 5.28 | 26.8 | 5.08 | M |
| 11 | Me | H | 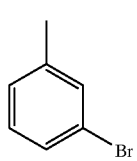 3-Br | H | (+/−) | — | 128–129 | 0.781 | 45.6 | 58.4 | A |

TABLE III-continued
Biolocial Activities of Synthesized Sultams
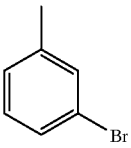
| No. | $R^N$ | $R^O$ | Ring C | $R^A$ | Config. | Opt. Rot. (deg.) | mp (deg. C.) | $EC_{50}$ ($\mu M$) | $IC_{50}$ ($\mu M$) | $TI_{50}$ | Act.[1] |
|---|---|---|---|---|---|---|---|---|---|---|---|
| 12 | Me | H | 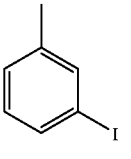 | H | (+)-(S) | 140 | 157 | 0.074 | 101 | 136.5 | A |
| 13 | Me | H | 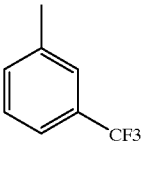 | H | (+)-(S) | 126 | 156 | 0.076 | 62.4 | 817 | A |
| 14 | Me | H | 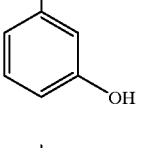 | H | (+/−) | — | 97–98 | 0.653 | 48 | 73.5 | A |
| 15 | Me | H | 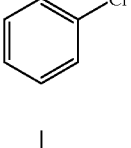 | H | (+/−) | — | 155–156 | 38.7 | >30 | >1.3 | M |
| 16 | Me | H | 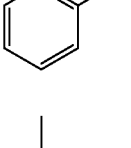 | H | (+/−) | — | 156 | 0.093 | >11 | >119 | A |
| 17 | Me | H | 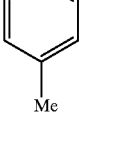 | H | (+)-(S) | 155 | 152 | 4.68 | 123 | 26.3 | M |
| 18 | Me | H |  | H | (+)-(S) | 131 | 128–129 | 1.53 | 138 | 90.4 | A |

TABLE III-continued
Biolocial Activities of Synthesized Sultams
| No. | $R^N$ | $R^O$ | Ring C | $R^A$ | Config. | Opt. Rot. (deg.) | mp (deg. C.) | $EC_{50}$ ($\mu$M) | $IC_{50}$ ($\mu$M) | $TI_{50}$ | Act.[1] |
|---|---|---|---|---|---|---|---|---|---|---|---|
| 19 | Me | H |  | H | (−)-(R) | −127 | 126–127 | — | — | — | I |
| 20 | Me | H | 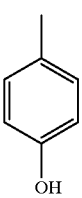 | H | (+/−) | — | 183 | — | >200 | — | I |
| 21 | Me | H | 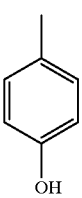 | H | (+)-(S) | 102 | 178–180 | — | >200 | — | I |
| 22 | Me | H | 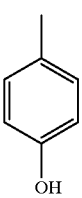 | H | (−)-(R) | −105 | 178–179 | — | >200 | — | I |
| 23 | Me | H | 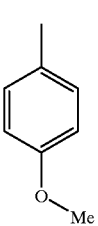 | H | (+)-(S) | 119 | 166–167 | — | >200 | — | I |

TABLE III-continued
Biolocial Activities of Synthesized Sultams
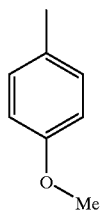
| No. | $R^N$ | $R^O$ | Ring C | $R^A$ | Config. | Opt. Rot. (deg.) | mp (deg. C.) | $EC_{50}$ ($\mu$M) | $IC_{50}$ ($\mu$M) | $TI_{50}$ | Act.[1] |
|---|---|---|---|---|---|---|---|---|---|---|---|
| 24 | Me | H | 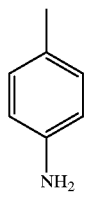 | H | (−)-(R) | −120 | 166 | — | >200 | — | I |
| 25 | Me | H | 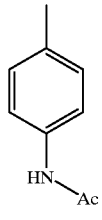 | H | (+/−) | — | 219–220 | 65 | >200 | >3.08 | I |
| 26 | Me | H | 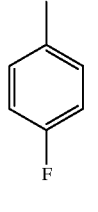 | H | (+/−) | — | 221 | — | >200 | — | I |
| 27 | Me | H | 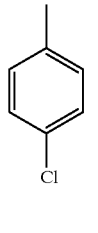 | H | (+/−) | — | 111–112 | 37.5 | 161 | 4.29 | M |
| 28 | Me | H |  | H | (+/−) | — | 132–133 | 19.6 | 29 | 1.48 | I |

TABLE III-continued
Biolocial Activities of Synthesized Sultams
| No. | $R^N$ | $R^O$ | Ring C | $R^A$ | Config. | Opt. Rot. (deg.) | mp (deg. C.) | $EC_{50}$ ($\mu$M) | $IC_{50}$ ($\mu$M) | $TI_{50}$ | Act.[1] |
|---|---|---|---|---|---|---|---|---|---|---|---|
| 29 | Me | H | 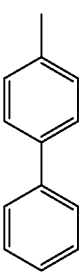 | H | (+/−) | — | 135 | 11.02 | 36.8 | 3.34 | M |
| 30 | Me | H | 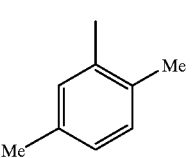 | H | (+/−) | — | 188 | — | >200 | — | I |
| 31 | Me | H | 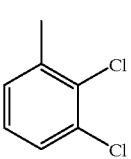 | H | (+/−) | — | 168–169 | 0.512 | >200 | >390 | A |
| 32 | Me | H | 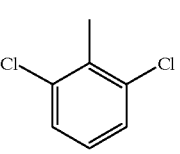 | H | (+/−) | — | 160–161 | 0.039 | >200 | >51.2 | A |
| 33 | Me | H | 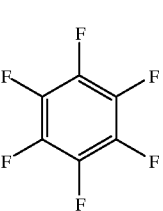 | H | (+/−) | — | 181–183 | 5.09 | 10.9 | 2.13 | M |
| 34 | Me | H |  | H | (+/−) | — | 154 | 40.2 | >198 | >4.93 | M |

TABLE III-continued

Biolocial Activities of Synthesized Sultams

| No. | R$^N$ | R$^O$ | Ring C | R$^A$ | Config. | Opt. Rot. (deg.) | mp (deg. C.) | EC$_{50}$ ($\mu$M) | IC$_{50}$ ($\mu$M) | TI$_{50}$ | Act.[1] |
|---|---|---|---|---|---|---|---|---|---|---|---|
| 35 | H | H | phenyl | H | (+/−) | — | — | — | — | — | — |
| 36 | H | H | 3-Cl-phenyl | H | (+/−) | — | 142–143 | 33.8 | 427 | 12.6 | M |
| 37 | Et | H | 3-Cl-phenyl | H | (+/−) | — | 100–101 | 0.167 | 39.7 | 238 | A |
| 38 | Bu | H | 3-Cl-phenyl | H | (+/−) | — | 116–117 | 1.35 | 18.2 | 13.5 | M |
| 39 | t-Bu | H | phenyl | H | (+/−) | — | 162 | — | >200 | — | I |
| 40 | Ph | H | phenyl | H | (+/−) | — | 168–169 | — | >200 | — | I |
| 41 | 2-Pr | H | phenyl | H | (+/−) | — | 141 | 3.23 | 244 | 75.4 | A |

TABLE III-continued
Biolocial Activities of Synthesized Sultams

| No. | $R^N$ | $R^O$ | Ring C | $R^A$ | Config. | Opt. Rot. (deg.) | mp (deg. C.) | $EC_{50}$ ($\mu M$) | $IC_{50}$ ($\mu M$) | $TI_{50}$ | Act.[1] |
|---|---|---|---|---|---|---|---|---|---|---|---|
| 42 | Me | Me | phenyl | H | (+/−) | — | 170 | 4.52 | 117 | 25.9 | A |
| 43 | Me | Me | 2-Cl-phenyl | H | (+/−) | — | — | — | — | — | — |
| 44 | Me | Me | 3-Cl-phenyl | H | (+/−) | — | 118–120 | 0.198 | 32.4 | 164 | A |
| 45 | Me | Me | 3-OH-phenyl | H | (+/−) | — | 191–192 | 30.7 | >200 | >6.5 | M |
| 46 | Me | $CF_3$ | phenyl | H | (+/−) | — | 138–139 | 0.46 | 31.8 | 69.1 | A |
| 47 | Me | H | phenyl | 5-Me | (+/−) | — | 165–167 | 31 | 156 | 5.03 | M |
| 48 | Me | H | 3-Cl-phenyl | 5-Me | (+/−) | — | — | — | — | — | — |

TABLE III-continued
Biolocial Activities of Synthesized Sultams
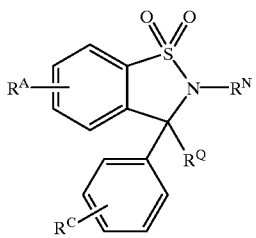
| No. | $R^N$ | $R^O$ | Ring C | $R^A$ | Config. | Opt. Rot. (deg.) | mp (deg. C.) | $EC_{50}$ ($\mu M$) | $IC_{50}$ ($\mu M$) | $TI_{50}$ | Act.[1] |
|---|---|---|---|---|---|---|---|---|---|---|---|
| 49 | Me | H | 4-F-phenyl | 5-Me | (+/−) | — | 94–95 | — | 76.9 | — | I |
| 50 | Me | H | 2-furyl | 5-Me | (+/−) | — | 151–152 | — | >200 | — | I |
| 51 | Me | H | 4-OH-phenyl | 5-Me | (+/−) | — | 210–211 | — | >140 | — | I |
| 52 | Me | H | 4-OMe-phenyl | 5-Me | (+/−) | — | 165–166 | — | >200 | — | I |
| 53 | Me | Me | phenyl | 5-Me | (+/−) | — | 148–149 | — | 107 | — | I |
| 54 | Me | H | phenyl | 5-Cl | (+/−) | — | 166–169 | 26.1 | >147 | 5.63 | M |

TABLE III-continued

Biolocial Activities of Synthesized Sultams

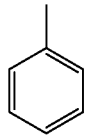

| No. | $R^N$ | $R^O$ | Ring C | $R^A$ | Config. | Opt. Rot. (deg.) | mp (deg. C.) | $EC_{50}$ ($\mu M$) | $IC_{50}$ ($\mu M$) | $TI_{50}$ | Act.[1] |
|---|---|---|---|---|---|---|---|---|---|---|---|
| 55 | Et | H | 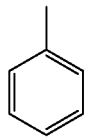 | 5-Cl | (+/−) | — | 112–114 | 19.3 | 60.6 | 3.14 | M |
| 56 | Pr | H | 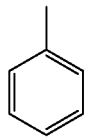 | 5-Cl | (+/−) | — | — | — | 365 | — | I |

[1]Activities are defined as per the NCI protocol:
A = "active";
M = "moderately active";
I = "inactive".
[2]Enantiomers were separated using a ChiralCel OD HPLC column. See Experimental for details.

The most potent compounds of the invention to alleviate HIV infections are the following compounds, the numerical reference being made to Table III.

Compound 4 wherein $R^A$ is hydrogen, $R^N$ is methyl, $R^Q$ is hydrogen and Ring C is 3-methylphenyl.

Compound 5 wherein $R^A$ is hydrogen, $R^N$ is methyl, $R^Q$ is hydrogen and Ring C is 3-methylphenyl, where the enantiomer is (+)-(S).

Compound 6 wherein $R^A$ is hydrogen, $R^N$ is methyl, $R^Q$ is hydrogen and Ring C is 3-fluorophenyl.

Compound 8 wherein $R^A$ is hydrogen, $R^N$ is methyl, $R^Q$ is hydrogen and Ring C is 3-chlorophenyl.

Compound 9 wherein $R^A$ is hydrogen, $R^N$ is methyl, $R^Q$ is hydrogen and Ring C is 3-chlorophenyl, where the enantiomer is (+)-(S).

Compound 11 wherein $R^A$ is hydrogen, $R^N$ is methyl, $R^Q$ is hydrogen and Ring C is 3-bromophenyl.

Compound 12 wherein $R^A$ is hydrogen, $R^N$ is methyl, $R^Q$ is hydrogen and Ring C is 3-bromophenyl, where the enantiomer is (+)-(S).

Compound 13 wherein $R^A$ is hydrogen, $R^N$ is methyl, $R^Q$ is hydrogen and Ring C is 3-iodophenyl, wherethe enantiomer is (+)-(S).

Compound 16 wherein $R^A$ is hydrogen, $R^N$ is methyl, $R^Q$ is hydrogen and Ring C is 2-chlorophenyl.

Compound 32 wherein $R^A$ is hydrogen, $R^N$ is methyl, $R^Q$ is hydrogen and Ring C is 2,3-dichlorophenyl.

Compound 37 wherein $R^A$ is hydrogen, $R^N$ is ethyl, $R^Q$ is hydrogen and Ring C is 3-chlorophenyl.

Compound 44 wherein $R^A$ is hydrogen, $R^N$ is methyl, $R^Q$ is methyl and Ring C is 3-chlorophenyl.

Compound 57 wherein $R^A$ is hydrogen, $R^N$ is methyl, $R^Q$ is hydrogen, and Ring C is 3-ethylphenyl.

Compound 58 wherein $R^A$ is hydrogen, $R^N$ is methyl, $R^Q$ is hydrogen, and Ring C is 3-vinylphenyl.

All compounds shown above are racemic mixtures except where otherwise specified. In all examples evaluated, the (+)-S enantiomers [except for examples, e.g., 3-(2-chlorophenyl, where Calin-Ingold-Prelog priorities are reversed)] and the chirality becomes (R) are the more active compounds of a pair of enantiomers.

It is to be noted that the term "inactive" refers only to the response in the Weislow protocol. These compounds are active in screening tests for inhibition of reverse transcriptase.

As is apparent from the teaching of the disclosure, a principal objective of the invention was to find compounds that exhibit very high activity in the Weislow protocol. However, other compounds other than those that excel in that activity, are expected to have biological activity that make them interesting candidates for biological applications other than as anti-HIV drugs.

Pharmaceutical Compositions

Pharmaceutical compositions that comprise one or more compounds of the invention may be formulated, as is well known in the prior art, such as by reference to known compilations as Remington's Pharmaceutical Sciences, Mack Publishing Co., Easton, Pa., USA. The dosage ranges for administration of the compounds of the invention are those needed to produce the desired affect without undue toxicity, whereby symptoms of infection are ameliorated.

The pharmaceutical composition may contain other pharmabiologically active compounds in a mixture with the compounds of the invention, to treat (therapeutically or prophylactically) acquired immunodeficiency syndrome (AIDS). For example, other active compounds may include, but are not limited to, other antiviral compounds (e.g., AZT, ddC, TIBO derivatives, acyclovir, alpha-interferon), immunostimulants (e.g., various interleukins and cytokines), immunomodulators and antibiotics (e.g., antibacterial, antifungal, anti-pneumocysitis agents), even when these do not show potent activity in the NCI Weislow protocol.

In addition, the compounds of the invention like HIV reverse transcriptases, are useful as tools and/or reagents to study inhibition of retroviral reverse transcriptases. Hence, the compounds are useful as a SAR (structure-activity relationships) tools to study, select and/or design other molecules to inhibit HIV.

The active compounds described herein are potentially useful in combination therapy with one or more of the compounds to provide an attractive regimen to halt proliferation of HIV under clinical conditions. Such agents include, but are not restricted to, inhibitors of HIV reverse transcriptase, e.g., AZT (zidovudine, Retrovir.RTM.), ddI (dideoxyinosine, didanosine, Videx.RTM.), d4T (dideoxydidehydrothymidine, stavudine), ddC (dideoxycytidine, zalcitabine), and nevirapine, among others. Combination regimens with HIV protease inhibitors might include, but are not restricted to, e.g., ritonavir (Norvir.RTM.) or saquinavir mesylate (Invirase.RTM.), efavirenz, a non-nucleoside reverse transcriptase inhibitor, (to be taken as part of combination therapy) among other drugs.

The preferred route of administration is oral, although other routes of administration are acceptable. The compounds may be mixed with inert materials for pharmaceutical efficacy as is known in the art. The compounds may be formulated in aqueous solution for intravenous (i.v.), intraperitoneal (i.p.), or subcutaneous (s.c.) administration. Topical applications include mixtures of the compounds with oils or fatty acid esters or as components of skin patches that are capable of delivering the drugs across the dermal layer. Aqueous solutions, or solutions in suitable carriers, could be administered intranasally.

The compounds of the invention readily lend themselves to being made part of what are called "inclusion compounds", such as with cyclodextrins and other suitable substances.

All publications referenced herein are hereby incorporated by reference in their entirety. The invention is not limited to the embodiments described herein, but encompasses all modifications with the scope of the following claims and equivalent thereof.

What is claimed is:

1. A method of synthesis of a sultam VI which comprises the steps of

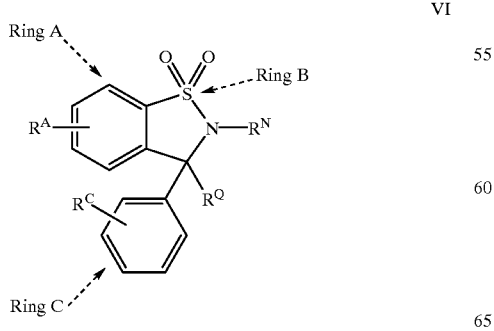

a) deprotonating the nitrogen and lithiating the ortho-position of an aryl sulfonamide in a resin-bound secondary sulfonamide of the structure I

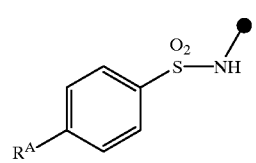

(where the black circle represents a solid synthetic resin and the sulfur of the sulfonamide is directly attached to the amine group of the resin) with an alkyl lithium in a ethereal solvent, alkylating the deprotonated secondary sulfonamide resin conjugate with an aromatic aldehyde or ketone II,

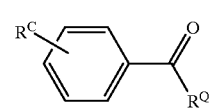

thereby obtaining a mixture of monoalkylated (III)

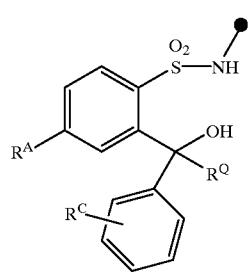

and bisalkylated (IV)

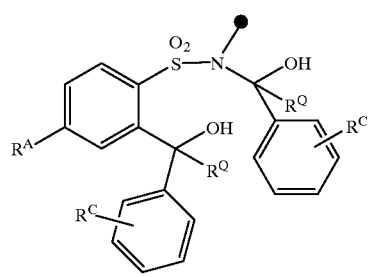

sulfonamide resin conjugates;

b) alkylating the mixture of monoalkylated (III) and bisalkylated (IV) sulfonamide resin conjugates by causing their deprotonation with a strong sterically hindered base, followed by the addition of an alkyl halide, thereby obtaining the tertiary sulfonamide resin conjugate V;

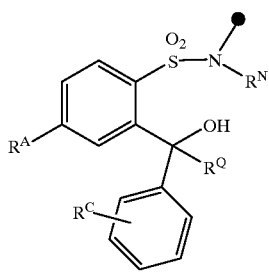

c) causing simultaneous ring closure and cleavage of the tertiary sulfonamide resin conjugate V by its reaction with a strong acid, thereby obtaining the sultam VI, and separating same, wherein the solid resin support is a synthetic resin which contains amino groups that undergo reactions steps (a) and (b), then in step (c) separate from the resin, concurrently forming stable carboncations, allowing ring closure to take place, wherein $R^A$ is a hydrogen, a linear or branched-chain lower alkyl, a halogen selected from the group consisting of chloro-, bromo-, iodo-, or fluoro; $R^N$ is a hydrogen, a linear or branched-chain lower alkyl; $R^Q$ is hydrogen, a linear or branched-chain lower alkyl, a substituted alkyl, aryl, alkyl-substituted aryl, mono or polycyclic, or heterocyclic, and $R^C$ is hydrogen, a linear or branched-chain lower alkyl, a halogen selected from the group consisting of chloro-, bromo-, iodo-, and fluoro; or hydroxyl, amine, lower alkoxy, amide, or alkyl substituted amide, wherein alkyl is alkyl, and wherein ring A is benzyl or is mono- or polycyclic of not more than three rings, or heterocycle where the heteroatoms are oxygen, nitrogen or sulfur; and ring C is benzyl, a mono- or polycyclic hydrocarbon providing a ketone or an aldehyde, or an aliphatic aldehyde.

2. The method of claim 1 wherein in sultam VI, $R^A$ is hydrogen or lower alkyl chloro-, $R^N$ is hydrogen, or lower alkyl; $R^Q$ is hydrogen, lower alkyl, $CF_3$, aryl, lower alkyl-substituted aryl; pyridinyl, picolinyl, naphthyl or quinolinyl; $R^C$ is hydrogen, lower alkyl, chloro-, bromo-, iodo- or fluoro; or acylamide.

3. The method of claim 2, wherein in sultam VI, $R^A$ is hydrogen, methyl or chloro-; $R^N$ is hydrogen, methyl, ethyl, propyl, isopropyl; $R^Q$ is hydrogen, methyl or phenyl; and $R^C$ is hydrogen, methyl, ethyl, vinyl, chloro-, bromo-, iodo-, fluoro-, $CF_3$, phenyl, methoxy or hydroxyl, furyl, acetamido or amino.

4. The method of claim 2 wherein the methyl or the chloro-substituent $R^A$ is on the 5-position on the A ring.

5. The method of claim 2 wherein the chloro-, fluoro-, bromo-, and iodo-substituents $R^C$ are on the 2-, 3- or 4-position of Ring C and the methyl, hydroxy, phenyl, furyl, methoxy, amino and the acetamido substituents are on the 3- or 4-position of Ring C.

6. The method of claim 3 wherein $R^A$ is hydrogen; $R^N$ is methyl; $R^Q$ is hydrogen; and $R^C$ is 2-chloro.

7. The method of claim 2 wherein $R^A$ is hydrogen; $R^N$ is methyl; $R^Q$ is hydrogen; and $R^C$ is 3-fluoro.

8. The method of claim 2 wherein $R^A$ is hydrogen; $R^N$ is methyl; $R^Q$ is hydrogen; and $R^C$ is 3-chloro.

9. The method of claim 2 wherein $R^A$ is hydrogen; $R^N$ is methyl; $R^Q$ is hydrogen; and $R^C$ is 3-bromo.

10. The method of claim 2 wherein $R^A$ is hydrogen; $R^N$ is methyl; $R^Q$ is hydrogen; and $R^C$ is 3-methyl.

11. The method of claim 2 wherein $R^A$ is hydrogen; $R^N$ is methyl; $R^Q$ is methyl; and $R^C$ is hydrogen.

12. The method of claim 2 wherein $R^A$ is hydrogen; $R^N$ is methyl; $R^Q$ is methyl; and $R^C$ is 3-chloro.

13. The method of claim 2 wherein $R^A$ is hydrogen; $R^N$ is isopropyl; $R^Q$ is hydrogen; and $R^C$ is hydrogen.

14. The method of claim 2 wherein $R^A$ and $R^Q$ are hydrogen, $R^C$ is 3-chloro, and $R^N$ is methyl and the sultam is the (S)-enantiomer.

15. The method of claim 2 wherein $R^A$ is hydrogen; $R^N$ is methyl; $R^Q$ is hydrogen; and $R^C$ is 3-fluoro and the sultam is the (S)-enantiomer.

16. The method of claim 2 wherein $R^A$ is hydrogen; $R^N$ is methyl; $R^Q$ is hydrogen; $R^C$ is 3-bromo and the sultam is the (S)-enantiomer.

17. The method of claim 2 wherein $R^A$ is hydrogen; $R^N$ is methyl; $R^Q$ is hydrogen; and $R^C$ is 3-methyl and the sultam is the (S)-enantiomer.

18. The method of claim 2 wherein $R^A$ is 5-chloro; $R^N$ is methyl; $R^Q$ is hydrogen; and $R^C$ is hydrogen.

19. The method of claim 2 wherein $R^A$ is 5-chloro; $R^N$ is ethyl; $R^Q$ is hydrogen; and $R^C$ is hydrogen.

20. The method of claim 2 wherein $R^A$ is hydrogen; $R^N$ is methyl; $R^Q$ is hydrogen; and $R^C$ is 4-fluoro or 4-bromo.

21. The method of claim 2 wherein $R^A$ is hydrogen; $R^N$ is methyl; $R^Q$ is hydrogen; and $R^C$ is 3-hydroxyl.

22. The method of claim 2 wherein $R^A$ is hydrogen; $R^N$ is methyl; $R^Q$ is methyl; and $R^C$ is 3-hydroxyl.

23. The method of claim 2 wherein $R^A$ is hydrogen; $R^N$ is methyl; $R^Q$ is hydrogen; and $R^C$ is 3-fluoro.

24. The method of claim 2 wherein in sultam VI
(1) $R^A$ is 5-methyl, $R^N$ is methyl, $R^Q$ is methyl and $R^C$ is hydrogen;
(2) $R^A$ is 5-methyl, $R^N$ is methyl, $R^Q$ is hydrogen and $R^C$ is 4-fluoro;
(3) $R^A$ is 5-methyl, $R^N$ is methyl, $R^Q$ is hydrogen and $R^C$ is 4-methoxy;
(4) $R^A$ is hydrogen, $R^N$ is methyl, $R^Q$ is hydrogen and $R^C$ is 4-methyl;
(5) $R^A$ is 5-methyl, $R^N$ is methyl, $R^Q$ is hydrogen and $R^C$ is H, wherein ring C is furyl.
(6) $R^A$ is 5-chloro, $R^N$ is propyl, $R^Q$ and $R^C$ are hydrogen;
(7) $R^A$ is hydrogen, $R^N$ is methyl, $R^Q$ is hydrogen, and $R^C$ is 4-phenyl;
(8) $R^A$ is hydrogen, $R^N$ is methyl, $R^Q$ is hydrogen and $R^C$ is 4-methoxy, and the sultam is the (S)-enantiomer;
(9) $R^A$ is hydrogen, $R^N$ is methyl, $R^Q$ is hydrogen and $R^C$ is 4-fluoro;
(10) $R^A$ is hydrogen, $R^N$ is methyl, $R^Q$ is hydrogen and $R^C$ is 4-methyl, and the sultam is the (S)-enantiomer;
(11) $R^A$ is hydrogen, $R^N$ is methyl, $R^Q$ and $R^C$ are hydrogen, and the sultam is the (−)-enantiomer;
(12) $R^A$ is hydrogen, $R^N$ is methyl, $R^Q$ is hydrogen and $R^C$ is 4-methyl, and the sultam is the (−)-enantiomer;
(13) $R^A$ is 5-methyl, $R^N$ is methyl, $R^Q$ is hydrogen, and $R^C$ is 3-hydroxyl;
(14) $R^A$ is hydrogen, $R^N$ is methyl, $R^Q$ is hydrogen and $R^C$ is 3-ethyl;
(15) $R^A$ is hydrogen, $R^N$ is methyl, $R^Q$ is hydrogen, and $R^C$ is 3-vinyl; and
(16) The substituents R are all hydrogens.

25. The process of claim 1 wherein the alkyl lithium is butyllithium, the alkylating aromatic aldehyde or ketone is benzaldehyde or acetophenone, respectively, the strong sterically hindered base to cause deprotonation is potassium tert-butoxide, the alkyl halide is iodomethane, and the strong acid that causes ring closure and cleavage is sulfuric or trifluoroacetic acid.

26. The process of claim 1 which is carried out by combinatorial organic synthesis which comprises the steps for synthesis of the sultams that are carried out to completion without purification of the intermediate products of intermediate stages.

27. A method for the synthesis of a sultam of formula VI that comprises the steps of reacting 2,4-(dimethoxyphenyl)-(4-methoxyphenyl)methylamine (VII),

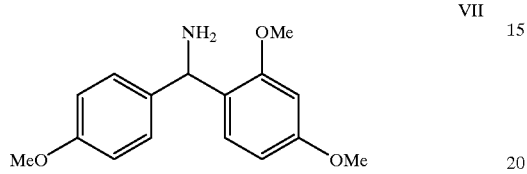

VII with benzenesulfonyl chloride in the presence of a base-forming sulfonamide VIII,

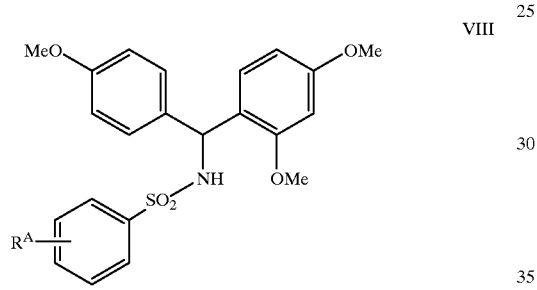

VIII deprotonating and lithiating of the sulfonamide VIII with subsequent addition of an aromatic aldehyde or a ketone yielding intermediates IX and X,

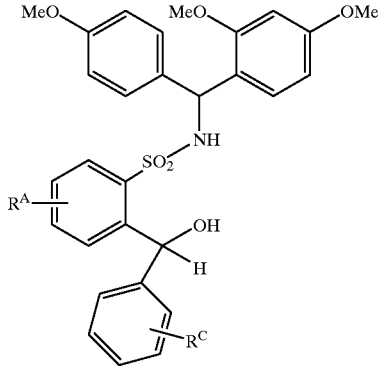

IX

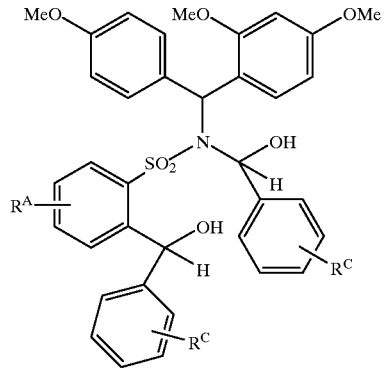

X deprotonating and adding of an alkyl halide, reacting the intermediate with a strong acid causing cleavage of the residue from an intermediate subsequent ring closure to yield a sultam of formula VI.

* * * * *